(12) United States Patent
Ciurczak et al.

(10) Patent No.: US 6,675,030 B2
(45) Date of Patent: Jan. 6, 2004

(54) NEAR INFRARED BLOOD GLUCOSE MONITORING SYSTEM

(75) Inventors: Emil W. Ciurczak, Goldens Bridge, NY (US); Kevin P. Bynum, Yonkers, NY (US); Howard Mark, Suffern, NY (US)

(73) Assignee: Euro-Celtique, S.A., Luxembourg (LU)

( * ) Notice: Subject to any disclaimer, the term of this patent is extended or adjusted under 35 U.S.C. 154(b) by 0 days.

(21) Appl. No.: 09/932,185

(22) Filed: Aug. 17, 2001

(65) Prior Publication Data

US 2002/0193671 A1 Dec. 19, 2002

Related U.S. Application Data

(60) Provisional application No. 60/226,637, filed on Aug. 21, 2000.

(51) Int. Cl.[7] ................................................ A61B 5/00
(52) U.S. Cl. ...................................................... 600/316
(58) Field of Search ................................. 600/300, 301, 600/310, 319, 316, 365; 128/903, 904

(56) References Cited

U.S. PATENT DOCUMENTS

| | | |
|---|---|---|
| 4,766,551 A | 8/1988 | Begley |
| 4,901,728 A | 2/1990 | Hutchison |
| 4,975,581 A | 12/1990 | Robinson et al. |

(List continued on next page.)

FOREIGN PATENT DOCUMENTS

| | | |
|---|---|---|
| EP | 0160768 | 11/1985 |
| EP | 0236023 | 9/1987 |
| EP | 0382908 | 8/1990 |
| EP | 0680727 | 11/1995 |
| EP | 0461207 | 2/1996 |
| EP | 0577684 | 5/1997 |
| EP | 0637217 | 3/1998 |
| WO | 9505599 | 2/1995 |
| WO | 9702781 | 1/1997 |
| WO | 9725915 | 7/1997 |
| WO | 9730629 | 8/1997 |
| WO | 9743947 | 11/1997 |
| WO | 9837805 | 9/1998 |
| WO | 9852469 | 11/1998 |
| WO | 9939631 | 2/1999 |
| WO | 9922639 | 5/1999 |
| WO | 9951142 | 10/1999 |

OTHER PUBLICATIONS

Harrington, P.B.; "Temperature–Constrained Backpropagation Neural Networks," *Analytical Chemistry*, vol. 66, No. 6, pp. 802–807(1994).

Savitsky, A and Golay, Marcel J.E.; "Smoothing and Differentiation of Data by Simplified Least Squares Procedures," *Analytical Chemistry*, vol. 36, No. 8, pp. 1627–1640 (1964).

(List continued on next page.)

*Primary Examiner*—Max F. Hindenburg
*Assistant Examiner*—David J. McCrosky
(74) *Attorney, Agent, or Firm*—Davidson, Davidson & Kappel, LLC

(57) ABSTRACT

An individualized modeling equation for predicting a patient's blood glucose values is generated as a function of non-invasive spectral scans of a body part and an analysis of blood samples from the patient, and is stored on a central computer. The central computer predicts a blood glucose value for the patient as a function of the individualized modeling equation and a non-invasive spectral scan generated by a remote spectral device. If the spectral scan falls within the range of the modeling equation, the predicted blood glucose level is output to the patient. If the spectral scan falls outside the range of the modeling equation, regeneration of the model is required, and the patient takes a number of noninvasive scans and an invasive blood glucose level determination. The computer regenerates the individualized modeling equation as a function of the set of spectral scans and corresponding blood glucose values.

23 Claims, 38 Drawing Sheets

U.S. PATENT DOCUMENTS

| | | |
|---|---|---|
| 5,009,230 A | 4/1991 | Hutchison |
| 5,028,787 A | 7/1991 | Rosenthal et al. |
| 5,068,536 A * | 11/1991 | Rosenthal .................. 600/316 |
| 5,070,874 A | 12/1991 | Barnes et al. |
| 5,077,476 A | 12/1991 | Rosenthal |
| 5,086,229 A | 2/1992 | Rosenthal et al. |
| 5,119,819 A | 6/1992 | Thomas |
| 5,121,338 A | 6/1992 | Lodder |
| 5,137,023 A | 8/1992 | Mendelson et al. |
| 5,139,023 A | 8/1992 | Stanley et al. |
| 5,140,985 A | 8/1992 | Schroeder et al. |
| 5,204,532 A | 4/1993 | Rosenthal |
| 5,206,701 A | 4/1993 | Taylor et al. |
| 5,223,714 A | 6/1993 | Maggard |
| 5,223,715 A | 6/1993 | Taylor |
| 5,242,602 A | 9/1993 | Richardson et al. |
| 5,243,546 A | 9/1993 | Maggard |
| 5,252,829 A | 10/1993 | Nygaard et al. |
| 5,258,825 A | 11/1993 | Reed et al. |
| 5,267,151 A | 11/1993 | Ham et al. |
| 5,267,152 A | 11/1993 | Yang et al. |
| 5,299,138 A | 3/1994 | Fiori et al. |
| 5,307,263 A | 4/1994 | Brown |
| 5,313,941 A | 5/1994 | Braig et al. |
| 5,343,044 A | 8/1994 | Sjaunja et al. |
| 5,348,002 A | 9/1994 | Caro |
| 5,348,003 A | 9/1994 | Caro |
| 5,349,188 A | 9/1994 | Maggard |
| 5,349,189 A | 9/1994 | Maggard |
| 5,360,972 A | 11/1994 | DiFoggio et al. |
| 5,361,758 A | 11/1994 | Hall et al. |
| 5,362,307 A | 11/1994 | Guy et al. |
| 5,370,114 A | 12/1994 | Wong et al. |
| 5,379,238 A | 1/1995 | Stark |
| 5,379,764 A | 1/1995 | Barnes et al. |
| 5,383,452 A | 1/1995 | Buchert |
| 5,433,197 A | 7/1995 | Stark |
| 5,435,309 A | 7/1995 | Thomas et al. |
| 5,446,681 A | 8/1995 | Gethner et al. |
| 5,456,252 A | 10/1995 | Vari et al. |
| 5,459,317 A | 10/1995 | Small et al. |
| 5,459,677 A | 10/1995 | Kowalski et al. |
| 5,481,476 A | 1/1996 | Windig |
| 5,498,875 A | 3/1996 | Obremski et al. |
| 5,512,751 A | 4/1996 | Murray, Jr. et al. |
| 5,515,847 A | 5/1996 | Braig et al. |
| 5,551,422 A | 9/1996 | Simonsen et al. |
| 5,568,400 A | 10/1996 | Stark et al. |
| 5,576,544 A | 11/1996 | Rosenthal |
| 5,582,168 A | 12/1996 | Samuels et al. |
| 5,602,755 A | 2/1997 | Ashe et al. |
| 5,606,164 A | 2/1997 | Price et al. |
| 5,610,836 A | 3/1997 | Alsmeyer et al. |
| 5,615,672 A | 4/1997 | Braig et al. |
| 5,638,816 A | 6/1997 | Kiani-Azarbayjany et al. |
| 5,641,962 A | 6/1997 | Perry et al. |
| 5,655,530 A | 8/1997 | Messerschmidt |
| 5,657,754 A | 8/1997 | Rosencwaig |
| 5,666,956 A | 9/1997 | Buchert |
| 5,668,373 A | 9/1997 | Robbat, Jr. et al. |
| 5,668,374 A | 9/1997 | DiFoggio et al. |
| 5,672,875 A | 9/1997 | Block et al. |
| 5,676,143 A | 10/1997 | Simonsen et al. |
| 5,680,320 A | 10/1997 | Helmer et al. |
| 5,680,321 A | 10/1997 | Helmer et al. |
| 5,692,504 A | 12/1997 | Essenpreis et al. |
| 5,706,208 A | 1/1998 | Osten et al. |
| 5,710,630 A | 1/1998 | Essenpreis et al. |
| 5,712,481 A | 1/1998 | Welch et al. |
| 5,712,797 A | 1/1998 | Descales et al. |
| 5,730,714 A | 3/1998 | Guy et al. |
| 5,740,073 A | 4/1998 | Bages et al. |
| 5,743,262 A | 4/1998 | Lepper, Jr. et al. |
| 5,747,806 A | 5/1998 | Khalil et al. |
| 5,750,994 A | 5/1998 | Schlager |
| 5,752,512 A | 5/1998 | Gozani |
| 5,771,891 A | 6/1998 | Gozani |
| 5,782,755 A | 7/1998 | Chance et al. |
| 5,788,632 A | 8/1998 | Pezzaniti et al. |
| 5,798,526 A | 8/1998 | Shenk et al. |
| 5,822,219 A | 10/1998 | Chen et al. |
| 5,823,951 A | 10/1998 | Messerschmidt |
| 5,823,966 A | 10/1998 | Buchert |
| 5,830,132 A | 11/1998 | Robinson |
| 5,830,133 A | 11/1998 | Osten et al. |
| 5,840,020 A * | 11/1998 | Heinonen et al. ........... 600/365 |
| 5,841,523 A | 11/1998 | Degen et al. |
| 5,857,462 A | 1/1999 | Thomas et al. |
| 5,890,489 A | 4/1999 | Elden |
| 5,896,198 A | 4/1999 | Chou et al. |
| 5,900,634 A | 5/1999 | Soloman |
| 5,910,109 A | 6/1999 | Peters et al. |
| 5,933,792 A | 8/1999 | Andersen et al. |
| 5,935,062 A | 8/1999 | Messerschmidt et al. |
| 5,945,676 A | 8/1999 | Khalil et al. |
| 5,946,128 A | 8/1999 | Paek |
| 5,946,640 A | 8/1999 | Goodacre et al. |
| 5,968,760 A | 10/1999 | Phillips et al. |
| 5,985,120 A | 11/1999 | Cholli et al. |
| 6,006,119 A | 12/1999 | Soller et al. |
| 6,012,019 A | 1/2000 | Saby |
| 6,014,577 A | 1/2000 | Henning et al. |
| 6,026,314 A | 2/2000 | Amerov et al. |
| 6,040,578 A | 3/2000 | Malin et al. |
| 6,049,082 A | 4/2000 | Methfessel |
| 6,061,582 A | 5/2000 | Small et al. |
| 6,064,065 A | 5/2000 | Block et al. |
| 6,064,897 A | 5/2000 | Lindberg et al. |
| 6,066,847 A | 5/2000 | Rosenthal |
| 6,067,463 A | 5/2000 | Jeng et al. |
| 6,070,128 A | 5/2000 | Descales et al. |
| 6,087,182 A | 7/2000 | Jeng et al. |
| 6,087,662 A | 7/2000 | Wilt et al. |
| 6,091,843 A | 7/2000 | Horesh et al. |
| 6,110,522 A | 8/2000 | Lepper, Jr. et al. |
| 6,114,699 A | 9/2000 | Barton et al. |
| 6,115,673 A | 9/2000 | Malin et al. |
| 6,124,134 A | 9/2000 | Stark |
| 6,137,108 A | 10/2000 | DeThomas et al. |
| 6,151,517 A | 11/2000 | Honigs et al. |
| 6,157,041 A | 12/2000 | Thomas et al. |
| 6,159,255 A | 12/2000 | Perkins |
| 6,161,028 A | 12/2000 | Braig et al. |
| 6,181,957 B1 | 1/2001 | Lambert et al. |
| 6,219,565 B1 | 4/2001 | Cupp et al. |
| 6,236,047 B1 | 5/2001 | Malin et al. |
| 6,309,884 B1 | 10/2001 | Cooper et al. |

OTHER PUBLICATIONS

Osborne, B.G., Fearn, T. and Hindle, P.H.; "Practical NIR Spectroscopy, With Applications in Food and Beverage Analysis," $2^{nd}$ Ed, Longman Scientific and Technical, pp. 114–116 (1993).

Draper, N. and Smith, H.; "Chapter 14 Dummy Variables," Applied Regression Analysis, $3^{rd}$ Ed, pp. 299–324 (1998).

Mark, H.; "Use of Mahalanobis Distances To Evaluate Sample Preparation Methods for Near–Infrared Reflectance Analysis," Analytical Chemistry, vol. 59, No. 5, pp. 790–795 (Mar. 1, 1987).

Mark, H.; "Normalized Distances for Qualitative Near–Infrared Reflectance Analysis," Analytical Chemistry, vol. 58, No. 2 pp. 379–384 (1986).

Mark, H. and Tunnell, D.; "Qualitative Near–Infrared Reflectance Analysis Using Mahalanobis Distances," *Analytical Chemistry*, vol. 57, No. 7, pp. 1446–1456 (Jun. 1985).

Honigs, D.E., Hieftje, G.M., Mark, H.L., Hirschfeld, T.B.; "Unique–Sample Selection via Near–Infrared Spectral Subtraction," *Analytical Chemistry*, vol. 57, No. 12, pp. 2299–2303 (Oct. 1985).

Conway, J.M., Norris, K.H., Bodwell, C.E.; "A new approach for the estimation of body composition: infrared interactance," *The American Journal of Clinical Nutrition* Vol 40, pp. 1123–1130 (1984).

Peuchant, E., Salles, C., Jensen, R.; "Determination of Serum Cholesterol by Near–Infrared Reflectance Spectrometry," *Analytical Chemistry*, vol. 59, No. 14, pp. 1816–1819 (Jul. 15, 1987).

Small, G.W., Arnold, M.A., Marquardt, LA.; "Strategies for Coupling Digital Filtering with Partial Least–Squares Regression: Application to the Determination of Glucose in Plasma by Fourier Transform Near–Infrared Spectroscopy," *Analytical Chemistry*, vol. 65, pp. 3279–3289 (1993).

Kruggel W.G., et al., "Near–Infrared Reflectance Determineation to Fat, Protein, and Moisture in Fresh Meat," *J. Assoc. Off. Anal. Chem.*, vol. 64, No. 3, pp. 692–696 (1981).

Arnold, M.A., "Motivation for Developing Optical Sensors for Blood Electrolyte Measurement"; *Clinical Chemnistry*, vol. 37, No. 8, pp. 1319–1320 (1991).

Shengtian Pan, et al., "Near–Infrared Spectroscopic Measurement of Physiological Glucose Levels in Variable Matrices of Protein and Triglycerides", *Anal. Chem.*, vol. 68, No. 7, pp. 1124–1135 (Apr. 1, 1996).

Marquardt, Lois A., et al., "Near–Infrared Spectroscopic Measurement of Glucose in a Protein Matrix", *Analytical Chemistry*, vol. 65, No. 22, pp. 3271–3278 (Nov. 15, 1993).

Arnold, Mark A., et al., "Determination of Physiological Levels of Glucose in an Aqueous Matrix with Digitally Filtered Fourier Transform Near–Infrared Spectra", *Analytical Chemistry*, vol. 62, No. 14, pp. 1457–1464 (Jul. 15, 1990).

Zee, Van Der P., et al. "Simulation of the Point Spread Function for Light in Tissue by a Monte Carlo Method," *Department of Medical Physics and Bioengineering, University College Hospital, Shropshire House, Capper Street, London Wc1E 6JA, U.K.*, pp. 179–191.

Takada, M., et al., "Non–Invasive Near–Infrared Measurements of Human Arm Tissue In Vivo," *R&D Engineering–Spectrophotometric Instrument, Analytical Instrument Division, Shimadzu Corporation, Nakagyo–ku, Kyoto 604, and *Biophysics Division, Research Institute of Applied Electricity, Hokkaido University, Sapporo 060, Japan.*, pp. 301–304.

Heise, H.M., et al. "Noninvasive Blood Glucose Sensors Based on Near–Infrared Spectroscopy", *Artif Organs*, vol. 18, No. 6, pp. 439–447 (Nov. 6, 1994).

Glaister, D.H., "Current and Emergining Technology in G–Loc Detection: Noninvasive Monitoring of Cerebral Microcirculation Using Near Infrared", *Aviation, Space, and Environmental Medicine*, pp. 23–28 (Jan. 1988).

Burfeindt, J., et al., "Angewandte optische Untersuchungen im nahen Infrarot– und Rotbereich an Humanvollblut; Anwendungsbeispiele", *Biomedizinische Technik Band 30, Heft 1–2/1985*, pp. 18–23.

Muller, U.A., et al., "Non–invasive Blood Glucose Monitoring by Means of Near Infrared Spectroscopy: Methods for Improving the Reliability of the Calibration Models," *The International Journal of Artificial Organs*, vol. 20, pp. 285–290 (Nov. 5, 1997).

Arnold, Mark A., "Non–invasive Glucose Monitoring", *Current Opinion in Biotechnology*, 1996, 7:46–49.

Eggert, Hans R., et al., "Optical Properties of Human Brain Tissue, Meninges,m and Brain Tumors in the Spectral Range of 200 to 900 nm", *Neurosurgery*, vol. 21, No. 4, pp. 459–464 (1987).

Giannini, Ivo, et al., "Rat Brain Monitoring by Near–Infrared Spectroscopy; An Assessment of Possible Clincal Significance" *Physiol. Chem. Phys.*, 14, pp. 295–305 (1982).

Israel, Richard G., et al., "Validity of a Near–Infrared Spectrophotometry Device for Estimating Human Body Composition", *Research Quarterly for Exercise and Sport*, vol. 60, No. 4, pp. 379–383 (1989).

Blazek,, V., "Verhalten der menschlichen Haut gegenuber Elektromagnetischer Strahlung im Sichtbaren Und Nahen IR–Bereich", *Z. Rechtsmedizin 77*, 91–103 (1976).

van Toorenbergen, A.W., et al., "Measurement of Total Serum Protein by Near–Infrared Reflectance Spectroscopy," *J. Clin. Chem. Clin. Biochem.*, vol. 26, No. 4, pp. 209–211 (1988).

Ciurczak, E.W., et al., "Chapter II.B.2 Identification of Actoves in Multicomponent Pharmaceutical Dosage Forms Using Near–Infrared Reflectance Analysis;" *Molecular Spectroscopy Workbench*, pp. 89–109, John Wiley & Sons, Inc. (1998).

Ciurczak, E.W., et al., Chapter II.B.8 Analysis of Solid and Liquid Dosage Forms Using Near–Infrared Reflectance Spectroscopy *Molecular Spectroscopy Workbench*, pp. 143–149, John Wiley & Sons, Inc. (1998).

Ciurczak, E.W., et al., "Chapter II.C.1 Chemometrics: A Powerful Toolbox For UV/VIS Spectroscopy;" *Molecular Spectroscopy Workbench*, pp. 165–172, John Wiley & Sons, Inc. (1998).

Ciurczak, E.W., et al., "Chapter III.1 Purgamenta Inuit, Purgamenta Exiunt;" *Molecular Spectroscopy Workbench*, pp. 315–317, John Wiley & Sons, Inc. (1998).

Burns, D.A., et al., "Chapter 4 Commercial NIR Instrumentation," *Handbook of Near–Infrared Analysis*, pp. 37–51, Mracel Dekker, Inc. (1992).

Burns, D.A., et al., "Chapter 5 Process Analysis," *Handbook of Near–Infrared Analysis*, pp. 53–105, Mracel Dekker, Inc. (1992).

Burns, D.A., et al., "Chapter 6 Data Analysis: Multilinear Regression and Principal Component Analysis," *Handbook of Near–Infrared Analysis*, pp. 107–158, Mracel Dekker, Inc. (1992).

Burns, D.A., et al., "Chapter 7 Data Analysis: Calibration of NIR Instruments by PLS Regression," *Handbook of Near–Infrared Analysis*, pp. 159–180, Mracel Dekker, Inc. (1992).

Burns, D.A., et al., "Chapter 10 NIR Spectroscopy Calibration Basics," *Handbook of Near–Infrared Analysis*, pp. 247–280, Mracel Dekker, Inc. (1992).

Burns, D.A., et al., "Chapter 13 Qualitative Discriminant Analysis," *Handbook of Near–Infrared Analysis*, pp. 329–363, Mracel Dekker, Inc. (1992).

Burns, D.A., et al., "Chapter 20 NIR Analysis of Pharmaceuticals," *Handbook of Near–Infrared Analysis*, pp. 549–563, Mracel Dekker, Inc. (1992).

* cited by examiner

NEAR-INFRARED TRANSMITTANCE (NIT)

NEAR-INFRARED REFLECTANCE (NIR)

DIFFUSE REFLECTANCE TRANSFORMS

SECOND TRANSFORM:

| 1ST TRANSFORM | NULLSCORR | BASECO<br>RRIZ | NORMALIZ | FIRSTDRV | SECNDDRV | MULTSCAT | KUBLMUNKG | RATIO | MEANCNTR | SGDERIV1 | SGDERIV2 | ABS2REFL |
|---|---|---|---|---|---|---|---|---|---|---|---|---|
| NULLS     | 1 | 1 | 1 | 1 | 1 | 1 | 1 | 1 | 1 | 0 | 1 | 1 | 1 |
| BASECORR  | 0 | 0 | 1 | 1 | 1 | 0 | 0 | 1 | 1 | 0 | 1 | 1 | 1 |
| NORMALIZ  | 0 | 1 | 0 | 1 | 1 | 0 | 0 | 1 | 0 | 0 | 1 | 1 | 1 |
| FIRSTDRV  | 0 | 0 | 1 | 0 | 0 | 0 | 0 | 1 | 0 | 0 | 0 | 0 | 0 |
| SECNDDRV  | 0 | 0 | 1 | 0 | 0 | 0 | 0 | 1 | 0 | 0 | 0 | 0 | 0 |
| MULTSCAT  | 0 | 0 | 0 | 1 | 1 | 0 | 1 | 1 | 0 | 0 | 1 | 1 | 1 |
| KUBLMUNK  | 0 | 1 | 1 | 1 | 1 | 1 | 0 | 1 | 0 | 0 | 1 | 1 | 0 |
| SMOOTHNG  | 0 | 1 | 1 | 1 | 1 | 1 | 1 | 0 | 0 | 0 | 1 | 1 | 1 |
| RATIO     | 0 | 0 | 0 | 0 | 0 | 0 | 0 | 0 | 0 | 0 | 0 | 0 | 0 |
| MEANCNTR  | 0 | 0 | 0 | 0 | 0 | 0 | 0 | 0 | 0 | 0 | 0 | 0 | 0 |
| SGDERIV1  | 0 | 0 | 1 | 0 | 0 | 0 | 0 | 1 | 0 | 0 | 0 | 0 | 0 |
| SGDERIV2  | 0 | 0 | 1 | 0 | 0 | 0 | 0 | 1 | 0 | 0 | 0 | 0 | 0 |
| ABS2REFL  | 0 | 1 | 1 | 1 | 1 | 1 | 0 | 1 | 0 | 0 | 1 | 1 | 0 |

FIG. 19A

DIFFUSE REFLECTANCE RATIOS

DENOMINATOR TRANSFORM

| NUMERATOR TRANSFORM | NULLS | BASECORR | NORMALIZ | FIRSTDRV | SECNDDRV | MULTSCAT | KUBLMUNK | SMOOTHNG | RATIO | MEANCNTR | SGDERIV1 | SGDERIV2 | ABS2REFL |
|---|---|---|---|---|---|---|---|---|---|---|---|---|---|
| NULLS | 1 | 1 | 0 | 0 | 0 | 0 | 0 | 0 | 0 | 0 | 0 | 0 | 0 |
| BASECORR | 0 | 1 | 0 | 0 | 0 | 0 | 0 | 0 | 0 | 0 | 0 | 0 | 0 |
| NORMALIZ | 0 | 1 | 1 | 0 | 0 | 0 | 0 | 0 | 0 | 0 | 0 | 0 | 0 |
| FIRSTDRV | 1 | 0 | 0 | 1 | 0 | 0 | 0 | 0 | 0 | 0 | 0 | 0 | 0 |
| SECNDDRV | 1 | 0 | 0 | 0 | 1 | 0 | 0 | 0 | 0 | 0 | 0 | 0 | 0 |
| MULTSCAT | 0 | 1 | 0 | 0 | 0 | 1 | 0 | 0 | 0 | 0 | 0 | 0 | 0 |
| KUBLMUNK | 0 | 1 | 0 | 0 | 0 | 0 | 1 | 0 | 0 | 0 | 0 | 0 | 0 |
| SMOOTHNG | 0 | 1 | 0 | 0 | 0 | 0 | 0 | 1 | 0 | 0 | 0 | 0 | 0 |
| RATIO | 0 | 0 | 0 | 0 | 0 | 0 | 0 | 0 | 0 | 0 | 0 | 0 | 0 |
| MEANCNTR | 0 | 0 | 0 | 0 | 0 | 0 | 0 | 0 | 0 | 0 | 0 | 0 | 0 |
| SGDERIV1 | 1 | 0 | 0 | 0 | 0 | 0 | 0 | 0 | 0 | 0 | 1 | 0 | 0 |
| SGDERIV2 | 1 | 0 | 0 | 0 | 0 | 0 | 0 | 0 | 0 | 0 | 0 | 1 | 0 |
| ABS2REFL | 0 | 1 | 0 | 0 | 0 | 0 | 0 | 0 | 0 | 0 | 0 | 0 | 1 |

*FIG. 19B*

DIFFUSE TRANSMITTANCE TRANSFORMS

SECOND TRANSFORM:

| 1ST TRANSFORM | NULLS | BASECORR | NORMALIZ | FIRSTDRV | SECNDDRV | MULTSCAT | KUBLMUNK | SMOOTHNG | RATIO | MEANCNTR | SGDERIV1 | SGDERIV2 | ABS2REFL |
|---|---|---|---|---|---|---|---|---|---|---|---|---|---|
| NULLS    | 1 | 1 | 1 | 1 | 1 | 1 | 0 | 1 | 1 | 0 | 1 | 1 | 1 |
| BASECORR | 0 | 0 | 1 | 1 | 1 | 0 | 0 | 1 | 1 | 0 | 1 | 1 | 1 |
| NORMALIZ | 0 | 1 | 0 | 1 | 1 | 0 | 0 | 1 | 0 | 0 | 1 | 1 | 1 |
| FIRSTDRV | 0 | 0 | 1 | 0 | 0 | 0 | 0 | 1 | 0 | 0 | 0 | 0 | 0 |
| SECNDDRV | 0 | 0 | 1 | 0 | 0 | 0 | 0 | 1 | 0 | 0 | 0 | 0 | 0 |
| MULTSCAT | 0 | 0 | 0 | 1 | 1 | 0 | 0 | 1 | 0 | 0 | 1 | 1 | 1 |
| KUBLMUNK | 0 | 0 | 0 | 0 | 0 | 0 | 0 | 0 | 0 | 0 | 0 | 0 | 0 |
| SMOOTHNG | 0 | 1 | 1 | 1 | 1 | 1 | 0 | 0 | 0 | 0 | 1 | 1 | 1 |
| RATIO    | 0 | 0 | 0 | 0 | 0 | 0 | 0 | 0 | 0 | 0 | 0 | 0 | 0 |
| MEANCNTR | 0 | 0 | 0 | 0 | 0 | 0 | 0 | 0 | 0 | 0 | 0 | 0 | 0 |
| SGDERIV1 | 0 | 0 | 1 | 0 | 0 | 0 | 0 | 1 | 0 | 0 | 0 | 0 | 0 |
| SGDERIV2 | 0 | 0 | 1 | 0 | 0 | 0 | 0 | 1 | 0 | 0 | 0 | 0 | 0 |
| ABS2REFL | 0 | 1 | 1 | 1 | 1 | 1 | 0 | 1 | 0 | 0 | 1 | 1 | 0 |

*FIG. 20A*

DIFFUSE TRANSMITTANCE RATIOS

DENOMINATOR TRANSFORM

| NUMERATOR TRANSFORM | NULLS | BASECORR | NORMALIZ | FIRSTDRV | SECNDDRV | MULTSCAT | KUBLMUNK | SMOOTHNG | RATIO | MEANCNTR | SGDERIV1 | SGDERIV2 | ABS2REFL |
|---|---|---|---|---|---|---|---|---|---|---|---|---|---|
| NULLS     | 1 | 1 | 0 | 0 | 0 | 0 | 0 | 0 | 0 | 0 | 0 | 0 | 0 |
| BASECORR  | 0 | 1 | 0 | 0 | 0 | 0 | 0 | 0 | 0 | 0 | 0 | 0 | 0 |
| NORMALIZ  | 0 | 1 | 1 | 0 | 0 | 0 | 0 | 0 | 0 | 0 | 0 | 0 | 0 |
| FIRSTDRV  | 1 | 0 | 0 | 1 | 0 | 0 | 0 | 0 | 0 | 0 | 0 | 0 | 0 |
| SECNDDRV  | 1 | 0 | 0 | 0 | 1 | 0 | 0 | 0 | 0 | 0 | 0 | 0 | 0 |
| MULTSCAT  | 0 | 1 | 0 | 0 | 0 | 1 | 0 | 0 | 0 | 0 | 0 | 0 | 0 |
| KUBLMUNK  | 0 | 0 | 0 | 0 | 0 | 0 | 0 | 0 | 0 | 0 | 0 | 0 | 0 |
| SMOOTHNG  | 0 | 1 | 0 | 0 | 0 | 0 | 0 | 1 | 0 | 0 | 0 | 0 | 0 |
| RATIO     | 0 | 0 | 0 | 0 | 0 | 0 | 0 | 0 | 0 | 0 | 0 | 0 | 0 |
| MEANCNTR  | 0 | 0 | 0 | 0 | 0 | 0 | 0 | 0 | 0 | 0 | 0 | 0 | 0 |
| SGDERIV1  | 1 | 0 | 0 | 0 | 0 | 0 | 0 | 0 | 0 | 0 | 1 | 0 | 0 |
| SGDERIV2  | 1 | 0 | 0 | 0 | 0 | 0 | 0 | 0 | 0 | 0 | 0 | 1 | 0 |
| ABS2REFL  | 0 | 1 | 0 | 0 | 0 | 0 | 0 | 0 | 0 | 0 | 0 | 0 | 1 |

FIG. 20B

CLEAR TRANSMITTANCE TRANSFORMS

SECOND TRANSFORM:

| 1ST TRANSFORM | NULLS | BASECORR | NORMALIZ | FIRSTDRV | SECNDDRV | MULTSCAT | KUBLMUNK | SMOOTHNG | RATIO | MEANCNTR | SGDERIV1 | SGDERIV2 | ABS2REFL |
|---|---|---|---|---|---|---|---|---|---|---|---|---|---|
| NULLS    | 1 | 1 | 1 | 1 | 1 | 0 | 0 | 1 | 1 | 0 | 1 | 1 | 1 |
| BASECORR | 0 | 0 | 1 | 1 | 1 | 0 | 0 | 1 | 1 | 0 | 1 | 1 | 1 |
| NORMALIZ | 0 | 1 | 0 | 1 | 1 | 0 | 0 | 1 | 0 | 0 | 1 | 1 | 1 |
| FIRSTDRV | 0 | 0 | 1 | 0 | 0 | 0 | 0 | 1 | 0 | 0 | 0 | 0 | 0 |
| SECNDDRV | 0 | 0 | 1 | 0 | 0 | 0 | 0 | 1 | 0 | 0 | 0 | 0 | 0 |
| MULTSCAT | 0 | 0 | 0 | 0 | 0 | 0 | 0 | 0 | 0 | 0 | 0 | 0 | 0 |
| KUBLMUNK | 0 | 0 | 0 | 0 | 0 | 0 | 0 | 0 | 0 | 0 | 0 | 0 | 0 |
| SMOOTHNG | 0 | 1 | 1 | 1 | 1 | 0 | 0 | 0 | 0 | 0 | 1 | 1 | 1 |
| RATIO    | 0 | 0 | 0 | 0 | 0 | 0 | 0 | 0 | 0 | 0 | 0 | 0 | 0 |
| MEANCNTR | 0 | 0 | 0 | 0 | 0 | 0 | 0 | 0 | 0 | 0 | 0 | 0 | 0 |
| SGDERIV1 | 0 | 0 | 1 | 0 | 0 | 0 | 0 | 1 | 0 | 0 | 0 | 0 | 0 |
| SGDERIV2 | 0 | 0 | 1 | 0 | 0 | 0 | 0 | 1 | 0 | 0 | 0 | 0 | 0 |
| ABS2REFL | 0 | 1 | 1 | 1 | 1 | 0 | 0 | 1 | 0 | 0 | 1 | 1 | 0 |

*FIG. 21A*

CLEAR TRANSMITTANCE RATIOS

DENOMINATOR TRANSFORM

| NUMERATOR TRANSFORM | NULLS | BASECORR | NORMALIZ | FIRSTDRV | SECNDDRV | MULTSCAT | KUBLMUNK | SMOOTHNG | RATIO | MEANCNTR | SGDERIV1 | SGDERIV2 | ABS2REFL |
|---|---|---|---|---|---|---|---|---|---|---|---|---|---|
| NULLS    | 1 | 1 | 0 | 0 | 0 | 0 | 0 | 0 | 0 | 0 | 0 | 0 | 0 |
| BASECORR | 0 | 1 | 0 | 0 | 0 | 0 | 0 | 0 | 0 | 0 | 0 | 0 | 0 |
| NORMALIZ | 0 | 1 | 1 | 0 | 0 | 0 | 0 | 0 | 0 | 0 | 0 | 0 | 0 |
| FIRSTDRV | 1 | 0 | 0 | 1 | 0 | 0 | 0 | 0 | 0 | 0 | 0 | 0 | 0 |
| SECNDDRV | 1 | 0 | 0 | 0 | 1 | 0 | 0 | 0 | 0 | 0 | 0 | 0 | 0 |
| MULTSCAT | 0 | 0 | 0 | 0 | 0 | 0 | 0 | 0 | 0 | 0 | 0 | 0 | 0 |
| KUBLMUNK | 0 | 0 | 0 | 0 | 0 | 0 | 0 | 0 | 0 | 0 | 0 | 0 | 0 |
| SMOOTHNG | 0 | 1 | 0 | 0 | 0 | 0 | 0 | 1 | 0 | 0 | 0 | 0 | 0 |
| RATIO    | 0 | 0 | 0 | 0 | 0 | 0 | 0 | 0 | 0 | 0 | 0 | 0 | 0 |
| MEANCNTR | 0 | 0 | 0 | 0 | 0 | 0 | 0 | 0 | 0 | 0 | 0 | 0 | 0 |
| SGDERIV1 | 1 | 0 | 0 | 0 | 0 | 0 | 0 | 0 | 0 | 0 | 1 | 0 | 0 |
| SGDERIV2 | 1 | 0 | 0 | 0 | 0 | 0 | 0 | 0 | 0 | 0 | 0 | 1 | 0 |
| ABS2REFL | 0 | 1 | 0 | 0 | 0 | 0 | 0 | 0 | 0 | 0 | 0 | 0 | 1 |

FIG. 21B

DERIVATIVE SPACING:

SPACING = INT (n ^ 1.4), n = 1 : 10

NEAR INFRARED BLOOD GLUCOSE MONITORING SYSTEM

CROSS-REFERENCE TO RELATED APPLICATION

This application clams the benefit of U.S. Provisional Patent Application No. 60/226,637, filed Aug. 21, 2000, the entire disclosure of which is hereby incorporated by reference.

FIELD OF THE INVENTION

The present invention relates to the field of near infrared spectrometry for predicting patient blood glucose levels.

BACKGROUND OF THE INVENTION

There are roughly four million people in the United States currently diagnosed with Diabetes Mellitus. This disease causes blindness, loss of extremities, heart failure, and other complications over time. There is no "cure" for the disease, which is caused by either the failure of the pancreas to produce insulin or the body's inability to use insulin, but rather only treatment, most commonly with insulin injections in order to change the blood-glucose level.

The majority of patients with Type I diabetes, as well as people with Type II diabetes or diagnosed as pre-diabetic, need to frequently monitor their blood glucose levels, establishing an individual blood glucose profile in order to adjust diet, medication, exercise, or to lower the blood glucose while avoiding hypoglycemia (low blood-sugar). In well-regulated patients, two or three blood samples are tested for glucose daily and are usually sufficient. In new or difficult patients, or when monitoring for hypoglycemia is required, blood samples may be required in rapid (every few minutes) succession.

Tests for blood glucose levels consist of obtaining blood by venipuncture or pricking an extremity (usually a finger) to draw a drop of blood. This blood sample is inserted into an analytical device (e.g., Accu-Check®, Hemo-Cue®, Diasensor 1000®, Coming Express 550®, Roche Cobas Mira®, or Ektachem (R)DT60II Analyzer®). The device may be an electrochemical detector that monitors reaction of glucose oxidase with glucose in the blood. The current or voltage is measured, and resulting data is displayed as a concentration, typically milligrams per deciliter (mg/dL). Another means of measuring glucose is by measuring the absorbance of the reaction at 540 nm. It is often difficult, particularly in elderly or infant patients, to perform the necessary measurement, particularly when needed several times a day.

As a result, a need has developed for non-invasive techniques useable in predicting the concentration of blood glucose in the bloodstream of a patient. In this regard, a significant number of researchers have attempted over the past few decades to develop non-invasive glucose monitors using near-infrared (NIR) spectrometers.

Infrared spectrometry is a technique that is based upon the vibrational changes of the atoms of a molecule. In accordance with infrared spectrometry, an infrared spectrum is generated by transmitting infrared radiation through a sample of an organic substance and determining the portions of the incident radiation that are absorbed by the sample. An infrared spectrum is a plot of absorbance (or transmittance) against wavenumber, wavelength or frequency. Infrared radiation is radiation having a wavelength between about 750 nm and about 1000 $\mu$m. Near-infrared radiation is radiation having a wavelength between about 750 nm and about 2500 nm.

A variety of different types of spectrometers are known in the art such as grating spectrometers, FT (Fourier transformation) spectrometers, Hadamard transformation spectrometers, AOTF (Acousto Optical Tunable Filter) spectrometers, diode array spectrometers, filter-type spectrometers, scanning dispersive spectrometers and non-dispersive spectrometers.

Filter-type spectrometers, for example, utilize an inert solid heated to provide continuous radiation (e.g., tungsten filament lamp) to illuminate a rotating opaque disk, wherein the disk includes a number of narrow bandpass optical filters. The disk is then rotated so that each of the narrow bandpass filters passes between the light source and the sample. An encoder indicates which optical filter is presently under the light source. The filters filter light from the light source so that only a narrow selected wavelength range passes through the filter to the sample. Optical detectors are positioned so to as detect light that either is reflected by the sample (to obtain a reflectance spectra) or is transmitted through the sample (to generate a transmittance spectra). The amount of detected light is then measured and provides an indication of the amount of absorbance of the light by the substance under analysis.

Diode Array spectrometers use infrared emitting diodes (IREDs) as sources of near-infrared radiation. A plurality of (for example, eight) IREDs are arranged over a sample work surface to be illuminated for quantitative analysis. Near-infrared radiation emitted from each IRED impinges upon an accompanying optical filter. Each optical filter is a narrow bandpass filter that passes NIR radiation at a different wavelength. NIR radiation passing through the sample is detected by a detector (such as a silicon photodetector). The amount of detected light is then measured and provides an indication of the amount of absorbance of the light by the substance under analysis.

Acousto Optical Tunable Filter spectrometers utilize an RF signal to generate acoustic waves in a $TeO_2$ crystal. A light source transmits a beam of light through the crystal, and the interaction between the crystal and the RF signal splits the beam of light into three beams: a center beam of unaltered white light and two beams of monochromatic and orthogonally polarized light. A sample is placed in the path of one of the monochromatic beam detectors, which are positioned to detect light that either is reflected by the sample (to obtain a reflectance spectra) or is transmitted through the sample (to generate a transmittance spectra). The wavelength of the light source is incremented across a wavelength band of interest by varying the RF frequency. The amount of detected light is then measured and provides an indication of the amount of absorbance of the light by the substance under analysis.

In grating monochromator spectrometers, a light source transmits a beam of light through an entrance slit and onto a diffraction grating (the dispersive element) to disperse the light beam into a plurality of beams of different wavelengths (i.e., a dispersed spectrum). The dispersed light is then reflected back through an exit slit onto a detector. By selectively altering the path of the dispersed spectrum relative to the exit slit, the wavelength of the light directed to the detector can be varied. The amount of detected light is then measured and provides an indication of the amount of absorbance of the light by the substance under analysis. The width of the entrance and exit slits can be varied to compensate for any variation of the source energy with wavenumber.

A nondispersive infrared filter photometer is designed for quantitative analysis of various organic substances. The wavelength selector comprises: a filter as previously described to control wavelength selection; a source; and a detector. The instrument is programmed to determine the absorbance of a multicomponent sample at wavelengths and then to compute the concentration of each component.

As stated above, spectrometers have been used to measure the chemical composition of blood and, more particularly, blood glucose. The mean blood glucose level varies within a normal range of 70–120 mg/dL from person to person. For diabetics, these fluctuations can vary markedly, reaching values of 200–400 mg/dL within a very short time in accordance with their food intake, physical activity, a complication by another disease, or the like. The majority of patients with Type I diabetes, as well as people with Type II diabetes or diagnosed as pre-diabetic, need to frequently monitor their blood glucose levels, establishing an individual blood glucose profile in order to adjust diet, medication or exercise, or in order to lower the blood glucose while avoiding hypoglycemia (low blood-sugar). In well-regulated patients, two or three blood samples are tested for glucose daily and are usually sufficient. In new or difficult patients, or when monitoring for hypoglycemia is required, blood samples may be required in rapid (every few minutes) succession.

The major problems with non-invasive NIR blood glucose monitors are the high operating cost, a lack of reproducible results and difficulty in use. Hand-held instruments for home use fail in that the instruments do not consistently provide the correct assessment of blood glucose concentration over the entire length of time the instruments are used. These hand-held devices are calibrated with a one-time global modeling equation hard-wired into the instrument, to be used by all patients from time of purchase onward. The model does not provide for variations in the unique patient profile which includes such factors as gender, age or other existing disease states.

For example, U.S. Pat. No. 5,961,449 to Toida et al. purports to disclose a method and apparatus for non-invasive measurement of the concentration of glucose in the aqueous humor in the anterior aqueous chamber of the eyeball, and a method and apparatus for non-invasive measurement of the concentration of glucose in the blood in accordance with the concentration of glucose in the aqueous humor. Known near-infrared analytical techniques using multivarient analysis are utilized therein.

A number of patents including U.S. Pat. Nos. 5,703,364, 5,028,787, 5,077,476 and 5,068,536, all to Rosenthal, purport to describe an at-home testing near-infrared quantitative analysis instrument and method of non-invasive measurement of blood glucose by measuring near-infrared energy following interaction with venous or arterial blood or following transmission through a blood-containing body part. Questions have been raised about the accuracy of the instrument described in these patents and, to date, FDA approval for such an instrument has not been attained.

U.S. Pat. No. 5,574,283 to Quintana purports to describe a near-infrared quantitative analysis instrument for measuring glucose comprising an analysis instrument having a removable insert that facilitates positioning of an individual user's finger within the instrument according to the size of the user's finger.

U.S. Pat. No. 5,910,109 to Peters et al. allegedly describes a glucose measuring device for determining the concentration of intravascular glucose in a subject including: a light source having a wavelength of 650, 880, 940 or 1300 nm to illuminate the fluid; receptors associated with the light sources for receiving light and generating a transmission signal representing the light transmitted and adapted to engage a body part of a subject; and a signal analyzer, which includes a trained neural network for determining the glucose concentration in the blood of the subject. This reference purportedly also provides a method for determining the glucose concentration, which method includes calibration of a measuring device and setting of an operating current for illuminating the light sources during operation of the device. According to this patent, when a transmission signal is generated by receptors, the high and low values from each of the signals are stored in the device and are averaged to obtain a single transmission value for each of the light sources. The averaged values are then analyzed to determine the glucose concentration, which then is displayed.

U.S. Pat. No. 5,935,062 to Messerschmidt et al. purports to describe a specular control device that can discriminate between diffusely reflected light that is reflected from selected depths or layers within the tissue by receiving the diffusely reflected light that is reflected from a first layer or depth within the tissue, while preventing the remaining diffusely reflected light from reaching the spectroscopic analyzer. This patent allegedly describes a method for obtaining diffuse reflectance spectra from human tissue for the non-invasive measurement of blood analytes, such as blood glucose by collecting the infrared energy that is reflected from a first depth and rejecting the infrared energy that is reflected from a second.

U.S. Pat. No. 5,941,821 to Chou allegedly provides an apparatus for more accurate measurement of the concentration of a component in blood (e.g., glucose), including a source for irradiating a portion of the blood by heat-diffusion to generate acoustic energy propagating in a second medium over a surface of the blood in response to the irradiation, a detector for detecting the acoustic energy and for providing an acoustic signal in response to the acoustic energy, and a processor for determining the concentration of the component in response to the acoustic signal and characteristics of the component.

In all spectroscopic techniques, including those discussed above, calibration samples must be run before an analysis is conducted. In NIR spectroscopy, a modeling equation (often referred to as a calibration model) that reflects the individual patient's blood glucose profile is generated by scanning a number of blood glucose samples to generate a set of calibration data, and then processing the data to obtain the modeling equation.

In a static system with little interference, this calibration is required only once, and spectral prediction can be conducted without the need to rerun calibration samples. In the real world, this is an infrequent occurrence. Most systems that require study are dynamic and require frequent recalibration. The recalibration procedure involves scanning a set of calibration samples and analyzing those same samples with a primary technique, such as High Performance Liquid Chromatography (HPLC), to adjust the modeling equation.

In previous attempts to develop a near IR spectral device for blood glucose determination, a single static modeling equation was generated using a statistical population of test subjects. This single modeling equation was then "hard-wired" into the spectral sensing device and used for all test subjects. This has proven to be problematic since people display blood chemistry within a wide range of normal values, or abnormal values in the case of a disease state (e.g., diabetes), due to each person's combinations of water level, fat level and protein level, each of which cause variations in energy absorption. The variations in these constituents between different people make a universal calibration for diabetes patients unlikely, particularly because the amount of glucose in the body is less than one thousandth of these other constituents.

U.S. Pat. No. 5,507,288 to Bocker et al. purportedly describes a non-invasive portable sensor unit combined with an invasive analytical system that can contain an evaluation instrument capable of calibrating the results of the non-invasive system. The evaluation instrument of this patent contains only one calibration equation, and the disclosure does not contemplate recalculation of the equation or recalibration of the evaluation instrument over time. This can be problematic, since, because a patient's blood chemistry changes with time, the "permanent" calibration slowly, or even rapidly, begins giving incorrect predictions. Thus, the ability to correctly assess the amount of blood glucose deteriorates over time.

Throughout this application, various patents and publications are referred to. Disclosure of these publications and patents in their entirety are hereby incorporated by reference into this application to more fully describe the state of the art to which this invention pertains. In particular, the disclosure of commonly-owned and co-pending U.S. patent application Ser. No. 09/636,041, entitled Automated System And Method for Spectroscopic Analysis and filed on Aug. 10, 2000, is hereby incorporated by reference.

SUMMARY OF THE INVENTION

In order to accurately predict blood glucose levels using a noninvasive spectroscopic technique, a dynamic modeling equation is needed. A dynamic modeling equation is one that provides a way to recalculate the equation when the model no longer accurately reflects the patient's glucose profile. A dynamic model is accomplished by scanning the subject with a noninvasive spectroscopic blood glucose monitor and then using an invasive technique (e.g., venipuncture or a fingerstick) to obtain a constituent value to associate with the spectral data. This procedure must be repeated a number of times in order to obtain a sufficient number of spectral data scans and associated constituent values to develop a robust and accurate modeling equation for the individual patient. The frequency and amount of recalibration needed is dependent on the amount of variation in the individual subject's blood glucose values. To recalibrate, additional spectral scans and associated constituent values are obtained from the patient, and the modeling equation is regenerated using the original data along with the new data. In cases where the original data is found to be unsuitable (for example, due to significant change in the patient's condition), it may be necessary to discard the original data and obtain a fall set of new spectral scans and associated constituent values. However, even if this recalibration is required on a weekly basis, a significant reduction in the amount of invasive monitoring has been achieved.

A truly dynamic modeling equation would seemingly require a highly trained and experienced individual using an advanced statistics computer program to evaluate the modeling equation and to perform the mathematics required to maintain the modeling equation. It is impractical, however, to have a scientist directly consult with each patient to maintain his or her individual modeling equation. This is especially true if development of a hand-held, remote spectral device for home use is desired.

Although many attempts have been made to construct a spectral device that will monitor the amount of blood glucose in a non-invasive manner, some of which are discussed above, a major shortcoming in each of these previous attempts has been in the development of a robust dynamic modeling equation for the prediction of bloodglucose levels.

In accordance with the present invention, a dynamic modeling equation is provided that can predict the patient's blood glucose level using a noninvasive spectral scan obtained from a remote spectral device (preferably handheld). A spectral scan is obtained from a patient and sent to a central computer. A central computer stores the generated spectral scan along with a previously generated patient modeling equation for that patient. A resultant blood glucose level is calculated for that patient based on his or her individual modeling equation. If the spectral scan falls within the range of the modeling equation, a blood glucose value is predicted and the predicted blood glucose level is output to the patient. If the spectral scan falls outside the range of the modeling equation, regeneration of the model is required, and the patient is instructed to take a number of noninvasive scans, followed by an invasive blood glucose level determination. All of the data is then transferred to the central computer where the modeling equation is regenerated based on both the existing data points and the new data points. A preferred method for generating and updating the modeling equation is set forth in more detail below.

Preferably, the central computer uses a complex statistics computer program to generate a new modeling equation, thereby allowing for much of this task to be automated. A new modeling equation is generated as needed, for example in cases of a change in medical condition that affects the blood glucose levels or as instructed by the manufacturer (e.g., once a month).

The remote spectral device communicates with the central computer by any conventional mode of data transmission, such as a cellular data link, a telephone modem, a direct satellite link, or an Internet link. The remote spectral device may be directly linked to the invasive blood glucose monitor by an appropriate data connection, such as an RS233 data connection, but preferably both the sensor and monitor are contained in the same unit along with a handheld computer, similar to a PALM PILOT™. In certain embodiments, additional messages can be sent from the central computer to the remote spectral device, for example, reminders to the patient to obtain blood glucose levels or to take medication. It may also be desirable to include other data inputs from the patient, such as blood pressure, heart rate and temperature, which data will be transmittable from the remote spectral device to the central computer.

In further embodiments, the central processing unit further communicates the relevant information received from the patient and any instructions transmitted to the patient via the remote spectral device to the patient's doctor or hospital.

In one embodiment of the present invention, there is provided a method for predicting blood glucose values in a patient by: generating an individualized modeling equation for a patient as a function of non-invasive spectral scans of a body part of the patient and an analysis of blood samples from the patient, and storing the individualized modeling equation on a central computer; receiving from the patient a non-invasive spectral scan generated by a remote spectral device; predicting a blood glucose value for the patient as a function of the non-invasive spectral scan and the individualized modeling equation, and transmitting the predicted blood glucose value to the patient; determining that a regeneration of the individualized modeling equation is required, and transmitting a request for a set of non invasive spectral scans and a corresponding set of blood glucose values to the patient; acquiring a set of noninvasive spectral scans from the patient using the remote spectral device and a corresponding set of blood glucose values from a remote invasive blood glucose monitor; transmitting the set of spectral scans and corresponding blood glucose values to the central computer; and regenerating the individualized modeling equation as a function of the set of spectral scans and corresponding blood glucose values.

BRIEF DESCRIPTION OF THE DRAWINGS

FIGS. 19A–B are tables of transform pairs used when data is collected by diffuse reflectance, wherein FIG. 19A depicts the first transform versus second transforms, and FIG. 19B depicts the ratio transform pairs.

FIGS. 20A–B are tables of transform pairs used when data is collected by diffuse-transmittance, wherein FIG. 20A depicts the first transform versus second transforms, and FIG. 20B depicts the ratio transform pairs.

FIGS. 21A–B are tables of transform pairs used when data is collected by clear transmittance, wherein FIG. 21A depicts the first transform versus second transforms, and FIG. 21B depicts the ratio transform pairs.

FIG. 22 is a table of derivative spacing factors.

DETAILED DESCRIPTION OF PREFERRED EMBODIMENTS

Figure 1:
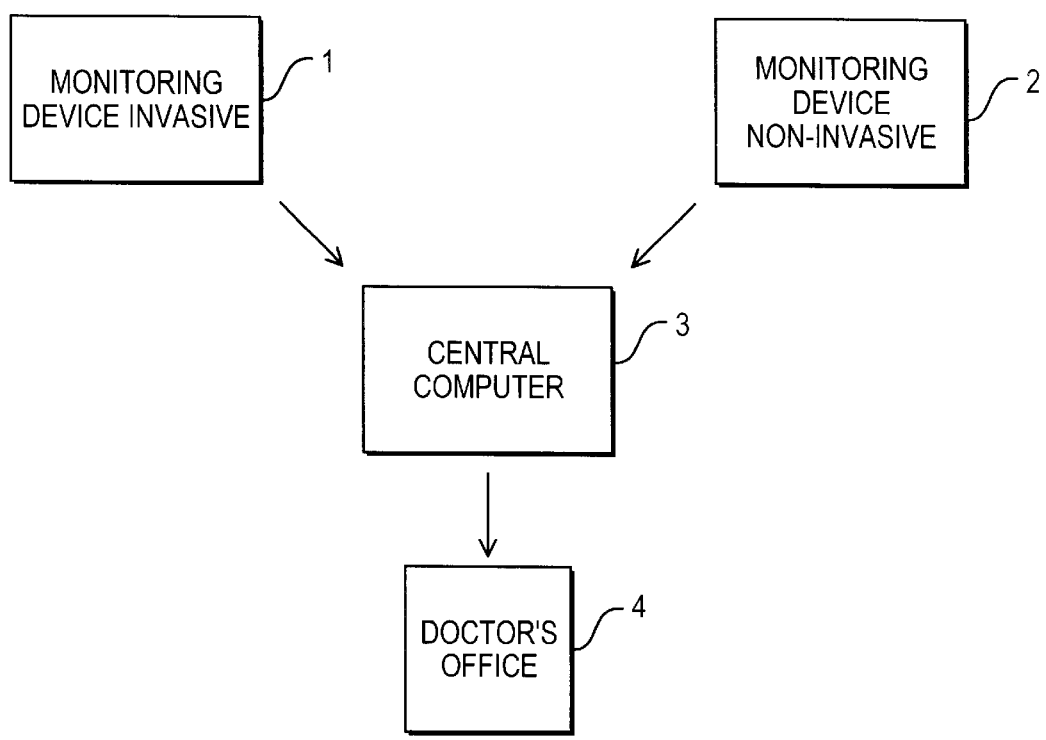
FIG. 1 is a simplified schematic showing the basic elements of the present invention and the interaction between the same.

In accordance with a preferred embodiment of the present invention, a system for non-invasive monitoring of blood glucose levels to create an individualized blood glucose profile is provided, wherein a patient can accurately predict the current status of his/her blood glucose levels and obtain immediate feedback on any corrective measures needed in the maintenance thereof. FIG. 1 sets forth the preferred interconnection between the various parts of a preferred embodiment of the present invention. A remote communication link is provided between a conventional invasive blood glucose monitoring device 1 (e.g., Accu-chek® blood glucose monitor or any other electrochemical analytical instrument), a non-invasive spectroscopic device 2 and a central computer 3. In certain embodiments, a further remote conunnunication link is provided between the central computer 3 and the primary doctor's office or hospital 4. The central computer stores the spectral scan from noninvasive device 2, the data obtained using invasive blood glucose monitor 1 and a modeling equation for each individual patient.

Initially, measurements of a patient's blood glucose levels are taken at predetermined intervals over a predetermined period of time using both the spectral device 2 and conventional invasive glucose monitoring methods. Intervals and sampling times as well as monitoring methods are well known to those of skill in the art. See, for example, Tietz, Norbert, *Fundamentals of Clinical Chemistry* (1976) Saunders Company, Philadelphia, Pa., pages 244–263. For each sample, one or more constituent values are measured by an invasive blood glucose monitoring method. In this regard, a constituent value is a reference value for blood glucose in the sample, which reference value is measured by an independent measurement technique comprising the use of an invasive method (e.g., Hemo-Cue® device). In this manner, the spectral data obtained by noninvasive means for each sample has associated therewith at least one constituent value for that sample.

The set of spectral scans (with its associated constituent values) is divided into a calibration subset and a validation subset. The calibration subset is selected to represent the variability likely to be encountered in the validation subset.

In accordance with a first embodiment of the present invention, a plurality of data transforms is then applied to the set of spectral scans. Preferably, the transforms are applied singularly and two-at-a-time. The particular transforms that are used and the particular combination pairs that are used are selected based upon the particular method that is being used to analyze the spectral data (e.g. diffuse reflectance, clear transmission, or diffuse transmission as discussed in the detailed description). Preferably, the plurality of transforms applied to the spectral data includes at least a second derivative and a baseline correction.

In accordance with a further embodiment of the present invention, transforms include, but are not limited to the following: performing a normalization of the spectral data, performing a ratio on the spectral data, performing a first derivative on the spectral data, performing a second derivative on the spectral data, performing a multiplicative scatter correction on the spectral data, and performing smoothing transforms on the spectral data. In this regard, it should be noted that both the normalization transform and the multiplicative scatter correction transform also inherently perform baseline corrections.

In accordance with a particularly preferred embodiment, the transforms are defined as follows:

The term NULL transform is defined, for the purposes of the present invention, as making no change to the data as originally collected.

The term NORMALIZ transform is defined, for purposes of the present invention, as a normalization transform (normalization). In accordance with this transform, the mean of each spectrum is subtracted from each wavelength's value for that spectrum, then each wavelength's value is divided by the standard deviation of the entire spectrum. The result is that each transformed spectrum has a mean of zero and a standard deviation of unity.

The term FIRSTDRV transform is defined, for purposes of the present invention, as performing a first derivative in the following manner. An approximation to the first derivative of the spectrum is calculated by taking the first difference between data at nearby wavelengths. A spacing parameter, together with the actual wavelength spacing in the data file, controls how far apart the wavelengths used for this calculation are. Examples of spacing parameters include but are not limited to the values 1, 2, 4, 6, 9, 12, 15, 18, 21 and 25. A spacing value of 1 (unity) causes adjacent wavelengths to be used for the calculation. The resulting value of the derivative is assumed to correspond to a wavelength halfway between the two wavelengths used in the computation. Since derivatives of wavelengths too near the ends of the spectrum cannot be computed, the spectrum is truncated to eliminate those wavelengths. If, as a result of wavelength editing or a prior data transform there is insufficient data in a given range to compute the derivative, then that range is eliminated from the output data. Preferably, the value of the spacing parameter is varied such that a FIRSTDRV transform includes a plurality of transforms, each having a different spacing parameter value.

The term SECNDDRV transform is defined, for purposes of the present invention, as performing a second derivative by taking the second difference (i.e., the difference between data at nearby wavelengths of the FIRSTDRV) as an approximation to the second derivative. The spacing parameters, truncation and other considerations described above with regard to the FIRSTDRV apply equally to the SECNDDRV. The second derivative preferably includes variable spacing parameters.

The term MULTSCAT transform is defined, for purposes of the present invention, as Multiplicative Scatter Correction. In accordance with this transform, spectra are rotated relative to each other by the effect of particle size on scattering. This is achieved for the spectrum of the i'th sample by fitting using a least squares equation $$Y_{iw} = a_i + b_i m_w$$

$$w = 1, \ldots, p$$

where $y_{iw}$ is the log $1/R$ value or a transform of the log $(1/R)$ value for the i'th sample at the w'th of p wavelengths and $m_w$ is the mean log $1/R$ value at wavelength w for all samples in the calibration set. If Multiplicative Scatter Correction (MSC) is applied to the spectra in the calibration set, then it should also be applied to future samples before using their spectral data in the modeling equation. It is the mean spectrum for the calibration set that continues to provide the standard to which spectra are fitted. The MSC may be applied to correction for log $1/R$ spectra or Kubelka-Munk data for example. See, Osborne, B. G., Feam, T. and Hindle, P. H., Practical NIR Spectroscopy, With Applications in Food and Beverage Analysis ($2^{nd}$ edition, Longman Scientific and Technical) (1993).

The term SMOOTHNG transform is defined, for purposes of the present invention, as a smoothing transform that averages together the spectral data at several contiguous wavelengths in order to reduce the noise content of the spectra. A smoothing parameter specifies how many data points in the spectra are averaged together. Examples of values for smoothing parameters include but are not limited to values of 2, 4, 8, 16 and 32. A smoothing value of 2 causes two adjacent wavelengths to be averaged together, and the resulting value of the smoothed data is assumed to correspond to a wavelength halfway between the two end wavelengths used in the computation. Since wavelengths too near the ends of the spectrum cannot be computed, the spectrum is truncated to eliminate those wavelengths. If, as a result of wavelength editing or a prior data transform, there is insufficient data in a given range to compute the smoothed value, then that range is eliminated from the output data. Preferably, the smoothing parameter value is varied such that a smoothing transform includes a plurality of smoothing transforms, each having a different smoothing parameter.

The term RATIO transform is defined, for purposes of the present invention, as a transform that divides a numerator by a denominator. The data to be used for numerator and denominator are separately and independently transformed. Neither numerator or denominator may itself be a ratio transform, but any other transform is permitted.

In any event, exemplary transform pairs that can be performed during the automatic search are described in FIGS. 19A (diffuse reflectance), 20A (diffuse transmittance) and 21A (clear transmittance). It should be noted that when "NULL" is selected for both transforms, the original data is used unchanged. The format of the original data is assumed by the system to be absorbency data (i.e., log 1T or log 1R).

In addition, exemplary combinations of transforms that can be used for the RATIO transform are illustrated in FIGS. 19B (diffuse reflectance), 20B (diffuse transmittance) and 21B (clear transmittance). If a ratio transform is specified, then numerator and denominator data sets are transformed individually.

In any event, one or more algorithms are then performed on the transformed and untransformed (i.e., Null transform) calibration data sets to obtain corresponding modeling equations for predicting the amount of blood glucose in a sample. Preferably, the algorithms include at least a multiple linear regression analysis (MLR calculations may, for example, be performed using software from The Near Infrared Research Corporation, 21 Terrace Avenue, Suffern, N.Y. 10901) and, most preferably, a Partial Least Squares and Principal Component Analysis as well.

The modeling equations are ranked to select a best model for analyzing the spectral data. In this regard, for each sample in the validation subset, the system determines, for each modeling equation, how closely the value returned by the modeling equation is to the constituent value(s) for the sample. The best modeling equation is the modeling equation that across all of the samples in the validation subset, returned the closest values to the constituent values: i.e., the modeling equation that provided the best correlation to the constituent values. Preferably, the values are ranked according to a Figure of Merit (described in equations 1 and 2 below).

The FOM is defined as $$\text{FOM (without Bias) } FOM = \sqrt{(SEE^2 + 2*SEP^2)/3} \qquad 1.$$

$$\text{FOM (with Bias) } FOM = \sqrt{(SEE^2 + 2*SEP^2 + W*b^2)/(3+W)} \qquad 2.$$

where SEE is the Standard Error of Estimate from the calculations on the calibration data, SEP is the Standard Error of Estimate from the calculations on the validation data, b is the bias of the validation data (bias being the mean difference between the predicted values and corresponding constituent values for the constituent) and W is a weighting factor for the bias. SEE is the standard deviation, corrected for degrees of freedom, for the residuals due to differences between actual values (which, in this context, are the constituent values) and the NIR predicted values within the calibration set (which, in this context, are the values returned by applying the spectral data in the calibration subset, which corresponds to the constituent values, to the modeling equation for which the FOM is being calculated). Similarly, SEP is the standard deviation for the residuals due to differences between actual values (which, in this context, are the constituent values) and the NIR predicted values outside the calibration set (which, in this context, are the values returned by applying the spectral data in the validation subset, which corresponds to the constituent values, to the modeling equation for which the FOM is being calculated).

The above referenced method of generating a best modeling equation is described in more detail in co-pending U.S. application Ser. No. 09/636,041, filed Aug. 10, 2000, which is incorporated by reference.

The best modeling equation is stored on the central computer, where this modeling equation is used to relate future noninvasive spectroscopic readings to a blood glucose level. Specifically, when the patient acquires a spectral scan using the remote noninvasive spectral device, the spectral scan is transmitted to the central computer where the modeling equation obtained for the individual patient is used to predict the blood glucose level from the spectral scan. If the spectral scan falls within the range of the modeling equation, the blood glucose level is output to the patient. If the spectral scan falls outside the range of the modeling equation, this is an indication that regeneration of the model is needed, and the patient is instructed to recalibrate the system by taking a number of spectral scans using the remote noninvasive spectral device and simultaneously taking a number of invasive measurements of the blood glucose level. The data obtained from the invasive and noninvasive techniques are transferred to the central computer, where a qualified technician supervises the reconstruction of the modeling equation based on the existing and new data points. Preferably, the central computer allows for much of this task to be automated in the manner described above.

Although the invasive blood glucose monitor and remote spectral device may be separate units capable of communicating with the central computer, preferably the invasive blood glucose monitor is capable of communicating the data obtained from the invasive patient blood samples to the remote spectral device, which in turn forwards this information to the central computer. Alternatively, the spectral data may be communicated to the invasive blood glucose monitor which in turn forwards this information onto the central computer. Information from both the spectral unit and invasive unit can be transmitted via any conventional mode of communication (e.g., a cellular data link, a telephone connection, a direct satellite link or an Internet link) to the central computer for analysis. Preferably, the remote spectral device is directly linked to the invasive blood glucose monitor by an appropriate data connection.

More preferably, the remote spectral device has a communication port, such as an RS232 communication port, that is connected to the invasive blood glucose monitor (e.g., an Accu-Check® blood glucose monitor). This allows constituent values from the invasive blood-monitoring device to be loaded directly onto the spectral sensing device.

In one embodiment, the invasive blood glucose monitor and remote spectral device, whether separate units or contained together in a single unit, are interfaced with a remote computer capable of communication with the central computer, for example a desktop workstation, laptop or a hand-held computer such as a PALM PILOT™. Communication between the invasive blood glucose monitor, the remote spectral device, the remote computer and the central computer can be implemented by any known mode of communication. Preferably, both the remote spectral device and the invasive blood glucose monitor have communication ports (such as a RS 232 port) that connect to the remote computer.

In another embodiment, the invasive blood glucose monitor and remote spectral device are contained within a single unit, preferably a portable unit containing a microprocessor and an associated communications interface for communicating with the central computer (similar in design to a PALM PILOT™ hand-held computer). Alternatively, the portable unit may be configured to communicate with a remote computer that, in turn, communicates with the central computer.

The portable unit or remote computer is preferably capable of receiving additional information from the patient for submission to the central computer via the transmission methods identified above. For example, it may be desirable to transmit further information from the patient such as a temperature, blood pressure, heart rate, patient exercise regimen or dietary regimen. In certain embodiments, the portable unit or remote computer is capable of storing the modeling equation and of performing the calculation of the glucose concentration information using the spectral data.

For an initial calibration of the system, any conventional method of invasive blood glucose monitoring may be used in conjunction with spectral scans obtained using the remote spectral device. For example, testing may be conducted in a doctor's office or hospital setting using venipuncture to withdraw blood from the patient at predetermined intervals. Such techniques can be accomplished with such commercially available instruments as the Diasensor 1000®, Coming Express 550®, Roche Cobas Mira® and Ektachem (R)DT60II Analyzer®. More preferably, blood measurements are obtained by the patient using a suitable self monitoring invasive glucose monitor, such as an Accu-Check® blood glucose monitor, a Yellow Springs Instrument® or a Hemo-Cue® blood glucose monitor. Generally, these invasive glucose monitors are electrochemical detectors that monitor reaction of glucose oxidase with glucose in the blood. The current or voltage is measured, and resulting data is displayed as concentration, typically in milligrams per deciliter (mg/dL). To use such a monitor, the patient draws blood from a finger tip using a lancet and places the blood on a chemical test strip that is then inserted into the monitor for analysis. Next, the instrument measures the glucose level in the blood and digitally displays the glucose level.

For noninvasive spectral scans conducted both for an initial calibration of the system and for regular monitoring of blood glucose levels, the remote spectral device is preferably attached to a body part, such as a finger, ear lobe, base of the thumb or other area of the body for which a diffuse reflectance scan in the spectral region of 500 nm to 3000 nm is taken. In certain preferred embodiments, the body part to be tested is the palm of the person's hand or the sole of the foot. It is thought that these body parts, which are less often subjected to direct sunlight and therefore tend to have fewer signs of sun damage such as freckling and tanning, may thereby provide more accurate results.

In order for the remote spectral device to be initially calibrated and an appropriate modeling equation for a particular patient to be obtained, measurements are conducted at predetermined intervals (e.g., morning and evening) over a predetermined period of time (e.g., 4–6 weeks) using both the remote noninvasive spectral device and the invasive blood glucose monitor. For example, in a suitable calibration schedule, the patient would obtain readings from both the remote spectral device and from the invasive blood glucose monitor once a week, over the course of a number of weeks (e.g., a five-week period of time). The information received by virtue of these readings is then forwarded to the central computer for storage and ultimately for use in the calibration of an appropriate algorithm (modeling equation) once sufficient data is received. It is also suitable for the calibration to be conducted in a doctor's office or in a hospital setting using the remote spectral device and a suitable invasive means for measuring blood glucose levels, with such information being sent to the central computer for storage of the information and for calculation of the modeling equation.

The modeling equation may be calculated by a scientist but preferably is conducted to large extent by the central computer, with a scientist overseeing and approving the results of the central computer's calculations. Most preferably, the modeling equation is generated by using a plurality of modeling equations that are generated in the manner described above. After a suitable modeling equation for the patient is determined, the equation is downloaded to the remote microprocessor (e.g., a remote computer or a processor that is integrated into the spectral device), where it is stored and used for predicting the blood glucose level of the patient until a new modeling equation becomes necessary (e.g., after the onset of a disease that affects blood glucose levels or at specified intervals). In other embodiments, the modeling equation is stored only in the central computer, and the spectral scan is merely transmitted to the central computer for analysis. Status checks of the system are conducted on a regular basis (e.g., every two to four weeks). To conduct the status checks, the patient simultaneously collects approximately five spectral scans and invasive blood glucose levels and sends them to the central computer for regeneration of a modeling equation. The five additional data points are added to the existing data, and a new modeling equation is generated using both the new and old data.

The prediction of the blood glucose value based on the spectral data using the algorithm may be conducted at the central computer or may be conducted by a remote computer associated with the remote spectral device or a processor integrated into the spectral device. If the calculation is conducted by the remote computer, the spectral information is nevertheless transmitted to the central computer for evaluation of the algorithm to ensure that recalibration is not needed, and preferably also for evaluation of blood glucose levels.

In certain preferred embodiments, the unit containing the remote spectral device will be able to detect other nonspectral body properties ("non-spectral compensation data"), such as pulse rate, blood pressure and body temperature, that may interfere with the blood glucose spectral prediction. In certain other embodiments, such non-spectral compensation data can be determined separately by the patient and then be input into the unit containing the remote spectral device or the remote computer via a suitable transmission mechanism, such as a key board or voice recognition program. In certain other embodiments, additional information of interest to the diabetic patient and doctor (such as food intake and exercise regimen) may be transmitted via the unit containing the remote spectral device or the remote computer to the central computer. In other embodiments, the nonspectral compensation data may be incorporated into the modeling equations as auxiliary or indicator variables. A discussion of how such variables can incorporated can be found in U.S. patent application Ser. No. 09/636,041.

In certain other embodiments, the remote spectral device may control a drug pump, which can automatically administer the appropriate amount of a drug to the patient such as by means of an IV line or pre-inserted subdermal pump.

The spectrometers contemplated for use in association with the present invention for use as the noninvasive spectral device can be any of the known versions in the art including, but not limited to, the devices described below and with respect to FIGS. 2–11. For example, spectrometers capable of being integrated into the remote spectral device include filter-type spectrometers, diode array spectrometers, AOTF (Acousto Optical Tunable Filter) spectrometers, grating spectrometers, FT (Fourier transformation) spectrometers, Hadamard transformation spectrometers and scanning dispersive spectrometers. Although the spectral device is preferably a handheld device including both the source of NIR radiation and the detector, larger instrumentation may also be suitable provided that the unit can easily be situated in the user's home and can be transported with the user when necessary. A detailed description of examples of several suitable spectrometers follows.

Figure 2A:
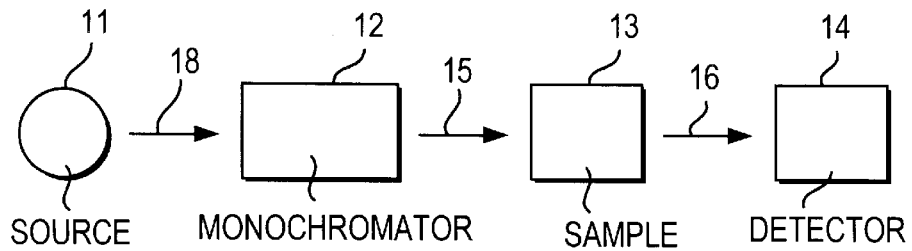
FIG. 2A is a basic schematic of transmittance spectrometer.
Figure 2B:
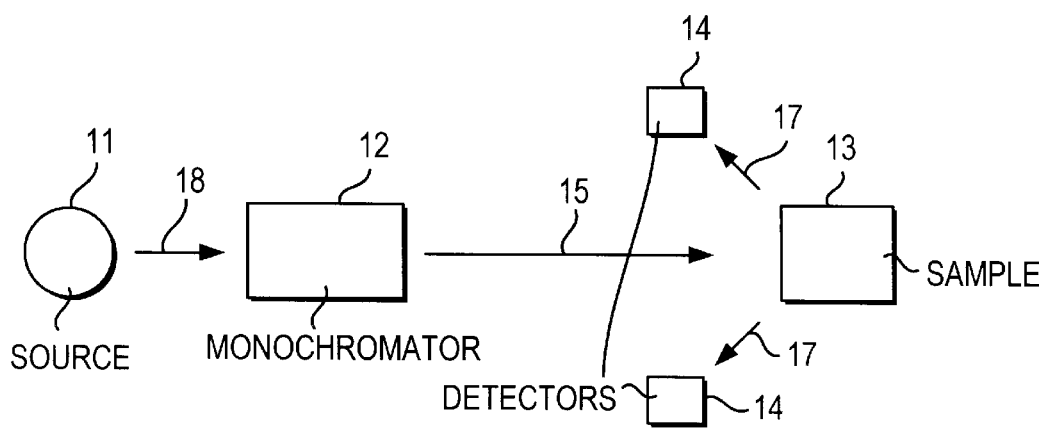
FIG. 2B is a basic schematic of reflectance spectrometer.

FIGS. 2A–B show the two most prevalent basic instrument designs common in modem near-infrared analysis: transmittance spectrometers and reflectance spectrometers. FIG. 2A is a basic schematic diagram of a transmittance spectrometer, and FIG. 2B is a basic schematic diagram of a reflectance spectrometer. In both cases, a monochromator 12 produces a light beam 15 having a desired narrow band of wavelengths from light 18 emitted from a light source 11, and the light beam 15 is directed onto a sample 13. However, in the case of a transmittance spectrometer, the detector(s) 14 are positioned to detect the light 16 that is transmitted through the sample 13, and, in the case of a reflectance spectrometer, the detector(s) 14 are positioned to detect the light 17 that is reflected off the sample 13. Depending upon its design, a spectrometer may or may not be used as both a transmittance and a reflectance spectrometer.

Reflectance measurements penetrate only 1–4 mm of the front surface of ground samples. This small penetration of energy into a sample brings about greater variation when measuring nonhomogeneous samples than do transmittance techniques.

The light source utilized in the remote spectral device is preferably a Quartz Tungsten Halogen bulb or an LED (Light Emitting Diode), although any suitable light source, including a conventional light bulb, may be used.

Suitable detectors for use in the analysis of the radiation include silicon (Si), indiumlantimony (InSb), indium/gallium/arsenic (InGaAs) and lead sulfide (PbS). In general, lead sulfide detectors are used for measurements in the 100–2500 -nm region, and lead sulfide "sandwiched" with silicon photodiodes are used for visible-near-infrared applications (typically 400–2600 nm).

Figure 3:
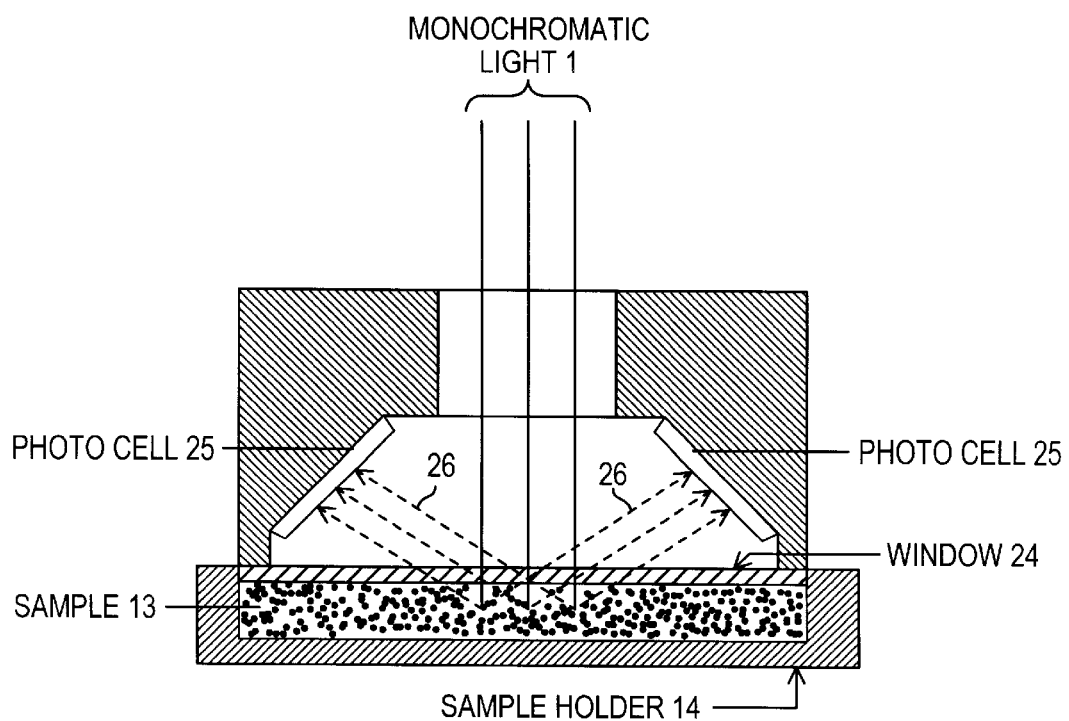
FIG. 3 is a diagram of an instrument detector system used for diffuse reflectance spectroscopy.

FIG. 3 is a diagram of an instrument detector system used for diffuse reflectance. The geometry of this system provides for monochromatic light 1 to illuminate the sample 13 (i.e., a body part of a patient such as the palm of the hand or the heel of the foot, or another sample that may be held by sample holder 14) at a 90° angle (normal incidence) to the sample. A window 24, through which the monochromatic light can pass, separates sample 13 from the detector. The collection detectors 26 comprise photo cells 25 for detecting the reflected light, each of which is at a 45° angle to window 24. Two or four detectors, each at a 45° angle, can be used.

Figure 4:
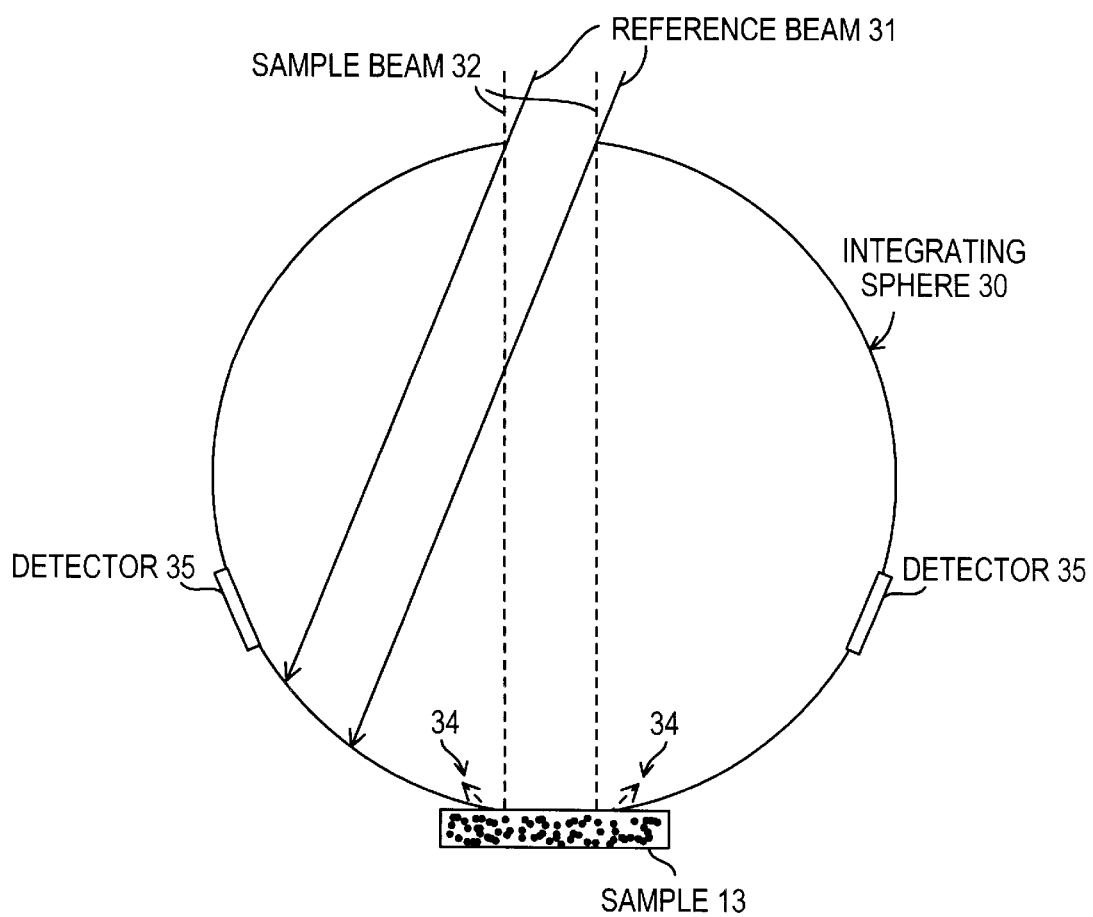
FIG. 4 is a schematic representation of diffuse reflectance using an integrating sphere sample presentation geometry.

In certain embodiments, the spectrometer may include an integrating sphere such as the one set forth in FIG. 4. In FIG. 4, a schematic representation of diffuse reflectance using an integrating sphere sample presentation geometry is shown. Within the integrating sphere 30 are shown a reference beam 31 and an illuminating beam 32 that hits the sample 13 and is deflected 34 off to the detectors 35. In early spectrometers, "sweet spots" existed on photomultiplier tubes of the detector and early semiconductor and photodiode detectors that made reproducible measurements using detectors very difficult, if not impossible. The integrating sphere cured this problem by protecting the detector from being susceptible to energy fluctuations from the incident beam because of deflection (scattering), refraction or diffraction of light when working in the transmittance mode. In modem applications, the use of the integrating sphere provides for internal photometric referencing, producing a sort of pseudo-double-beam instrument. Single-beam instruments must be set up to measure a reference material before or after the sample scans are taken, requiring inconvenience on the part of the user. For purposes of the present invention, there is no clear-cut advantage of using an integrating sphere over the diffuse reflectance 0–45 geometry. In fact, the 0–45 geometry often lends itself better to a transmittance measurement than do the integrating sphere systems.

Figure 5:
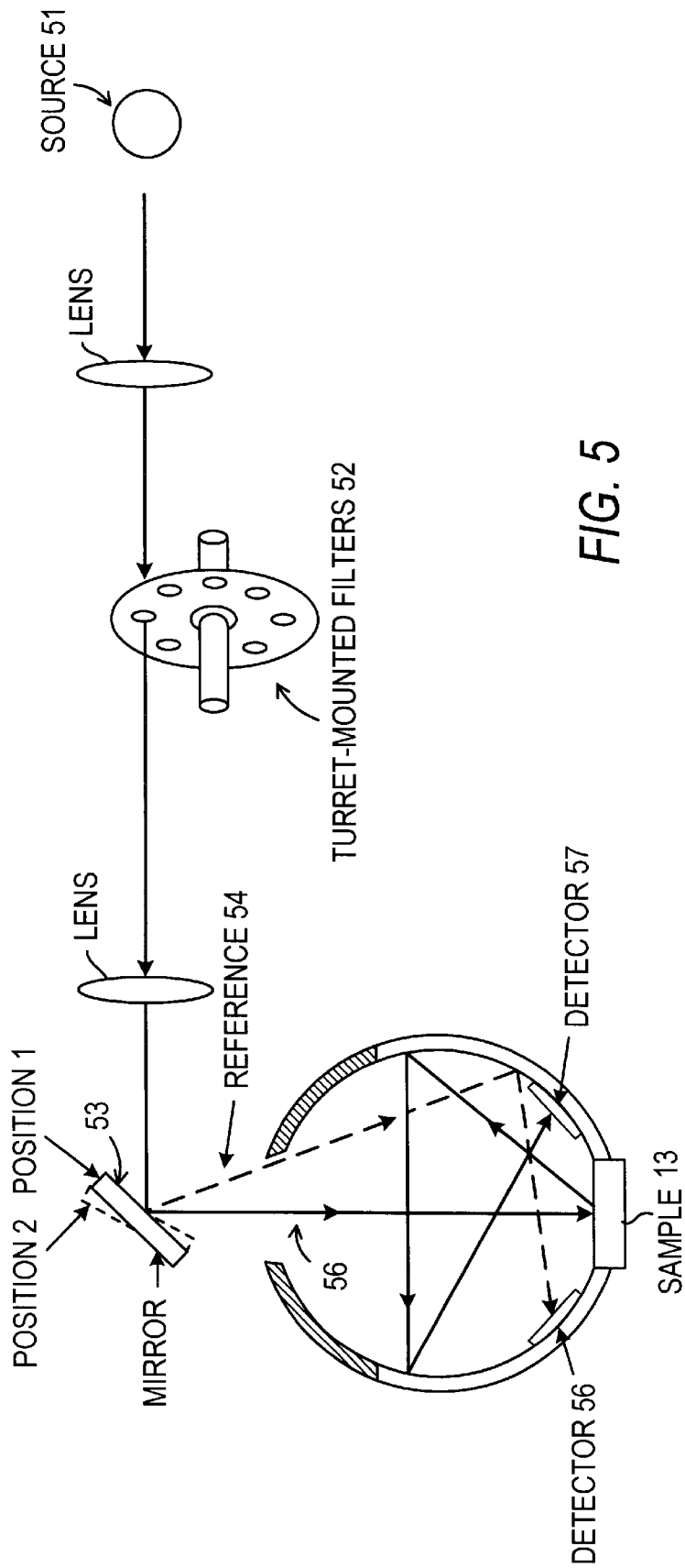
FIG. 5 is a diagram of a turret-mounted interference filter instrument.

FIG. 5 shows a split-beam spectrometer. Light is transmitted from the light source 51 through the filter 52 (which is shown as being turret-mounted) to a mirror 53 that is positioned to angle the light and create a split-beam, with one resulting beam 54 acting as a reference beam to a first detector 55 and a second resulting beam 56 passing through or reflecting off the sample 13 to a second detector 57. The difference in the amount of detected light at the second detector is compared to the amount of light at the first detector. The difference in the detected light is an indication of the absorbance of the sample.

Nondispersive infrared filter photometers are designed for quantitative analysis of various organic substances. The wavelength selector comprises: a filter, as previously described, to control wavelength selection; a source; and a detector. The instrument is programmed to determine the absorbance of a multicomponent sample at wavelengths and then to compute the concentration of each component.

Figure 6:
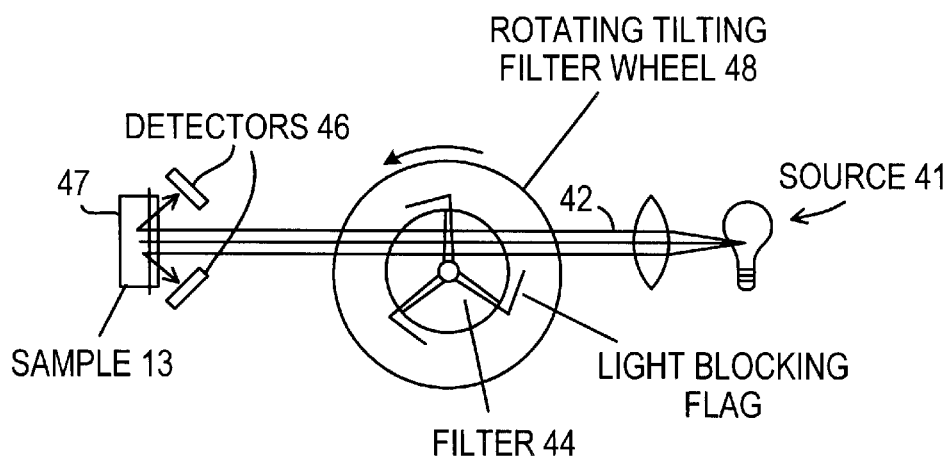
FIG. 6 shows a rotating tilting filter wheel utilizing wedge interference filters.
Figure 7:
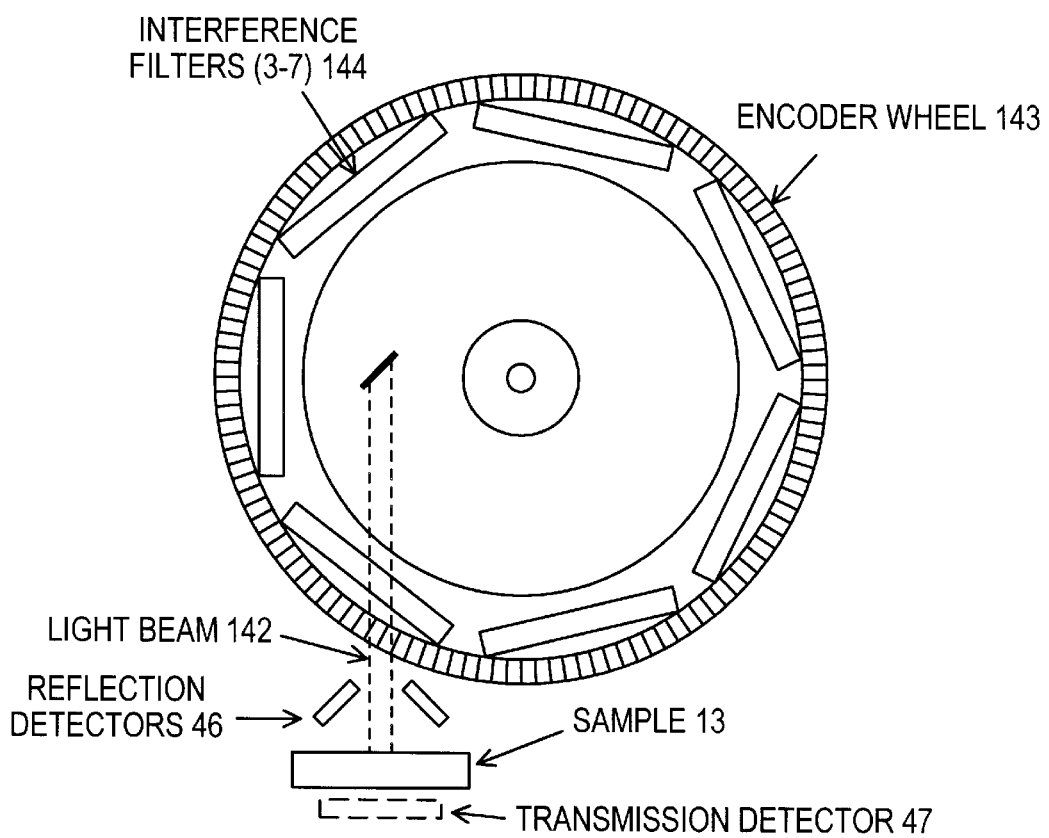
FIG. 7 shows a spinning filter system in which the light passes through an encoder wheel.

FIGS. 6 and 7 illustrate two basic forms of filter-type NIR spectrometer utilizing a tilting filter arrangement.

FIG. 6 shows a nondispersive infrared filter photometer designed for quantitative analysis of various organic substance. This device utilizes a light source 41, such as the conventional light bulb shown in the figure, to illuminate 42 a rotating opaque wheel 48, wherein the disk includes a number of narrow bandpass optical filters 44. The wheel is then rotated so that each of the narrow bandpass filters passes between the light source and a sample 13. The wheel 48 controls which optical filter 44 is presently before the light source. The filters 44 filter the light from the light source 41 so that only a narrow selected wavelength range passes through the filter to the sample 13. Optical detectors 46 are positioned to detect light that either is reflected by the sample (to obtain a reflectance spectra, as illustrated with detectors 46) or is transmitted through the sample (to generate a transmittance spectra, as illustrated with detector 47). The amount of detected light is then measured, thereby providing an indication of the amount of absorbance of the light by the substance under analysis.

FIG. 7 shows a rotating encoder wheel 143 utilizing wedge interference filters 144 for blocking light. Light 142 is transmitted through the encoder wheel 143 at varying wavelengths and bandpass, dependent on the incident angle of the light passing through the interference filter 144 to the sample 13. Optical detectors 46 are positioned to detect light that either is reflected by the sample (to obtain a reflectance spectra, as illustrated with detectors 46) or is transmitted through the sample (to generate a transmittance spectra, as illustrated with detector 47). The amount of detected light is then measured, providing an indication of the amount of absorbance of the light by the substance under analysis.

Figure 8A:
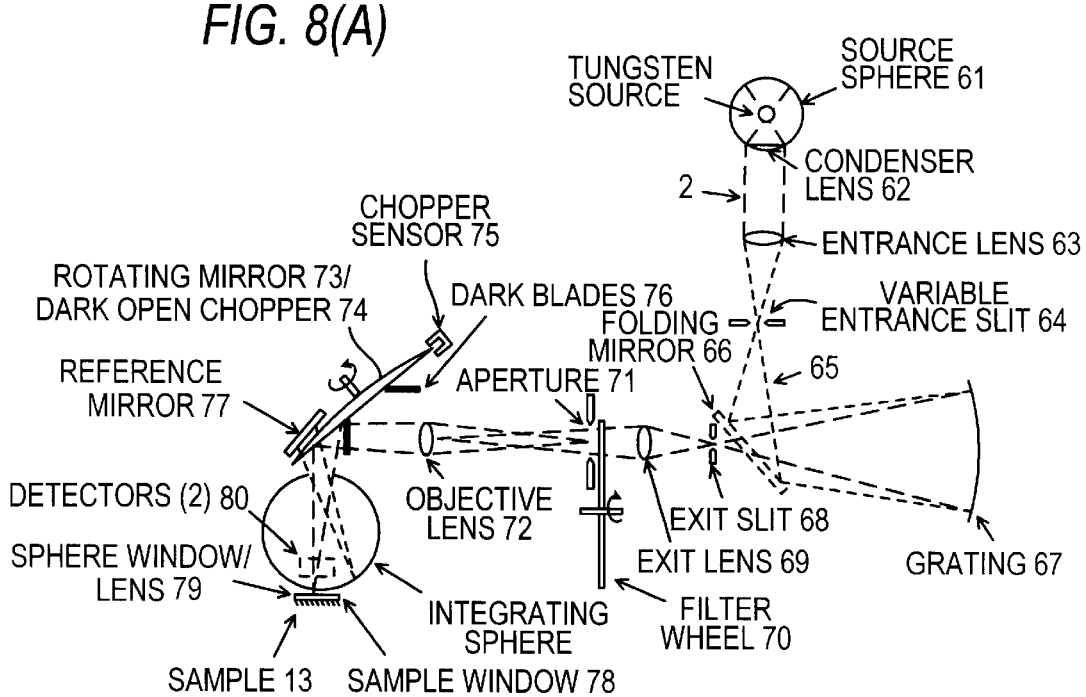
FIG. 8 is a diagram of a grating monochromator spectrometer, with FIG. 8A showing a side view and FIG. 8B a top view of the grating instrument.
Figure 8B:
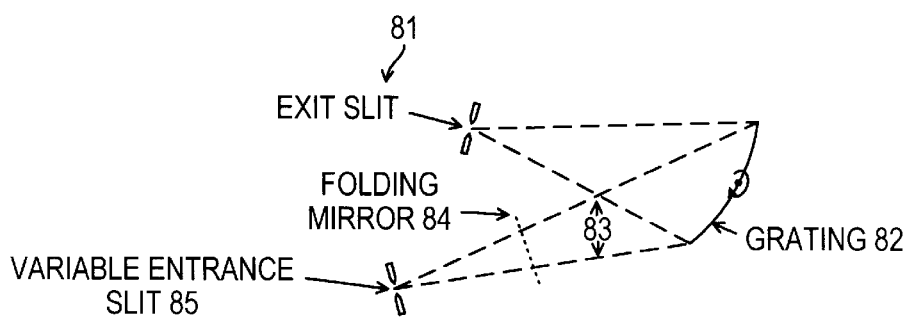

FIGS. 8A and 8B illustrate a grating monochrometer. In FIG. 8A, light is transmitted from a source 61 containing a condenser lens 62 through an entrance lens 63 to a variable entrance slit 64 where the beams of light 65 are deflected to a folding mirror 66. The mirror sends the beam of light to a grating 67, which in turn projects the light through an exit slit 68 to an exit lens 69. The light then passes through a filter wheel 70 containing aperatures 71 to an objective lens 72 and then on to a rotating mirror 73. The rotating mirror 73 has a dark/open chopper 74, a chopper sensor 75, a dark blade(s) 76 and a reference mirror 77 capable of sending a reference beam. The light is transmitted from the rotating mirror through a sphere window lens 79 and a sample window 78 to the sample 13, which then reflects the light to detector(s) 80. In FIG. 8(B) a top view of the grating instrument is shown, wherein light passes through the exit slit 81 to the grating 82 which projects the beam 83 to a folding mirror 84, from which it is projected to a variable entrance slit 85.

Figure 9:
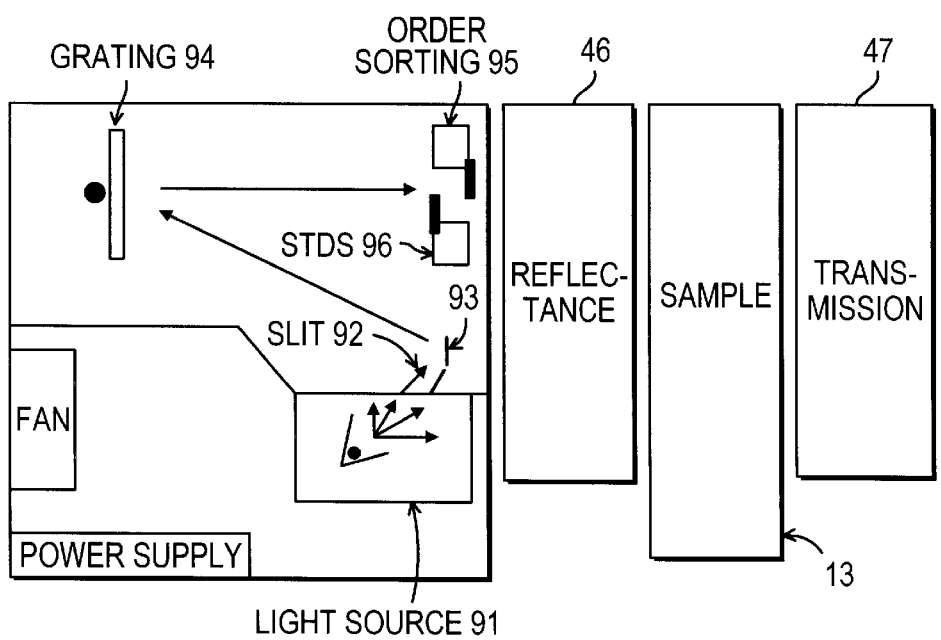
FIG. 9 shows a typical predispersive monochromator-based instrument in which the light is dispersed prior to striking the sample.

FIG. 9 shows a schematic diagram of typical pre-dispersive monochromator-based instrument in which the light is dispersed prior to striking the sample. As shown in FIG. 9, the light source 91 transmits a beam of light 92 through an entrance slit 93 and onto a grating 94. The grating 94 separates the light into a plurality of beams of different wavelengths. Via the order sorting 95 and stds 96 components, a desired band of wavelengths is selected for transmission to the sample 13. As illustrated, this spectrometer may also be used with both transmittance detectors and reflectance detectors 46.

Figure 10:
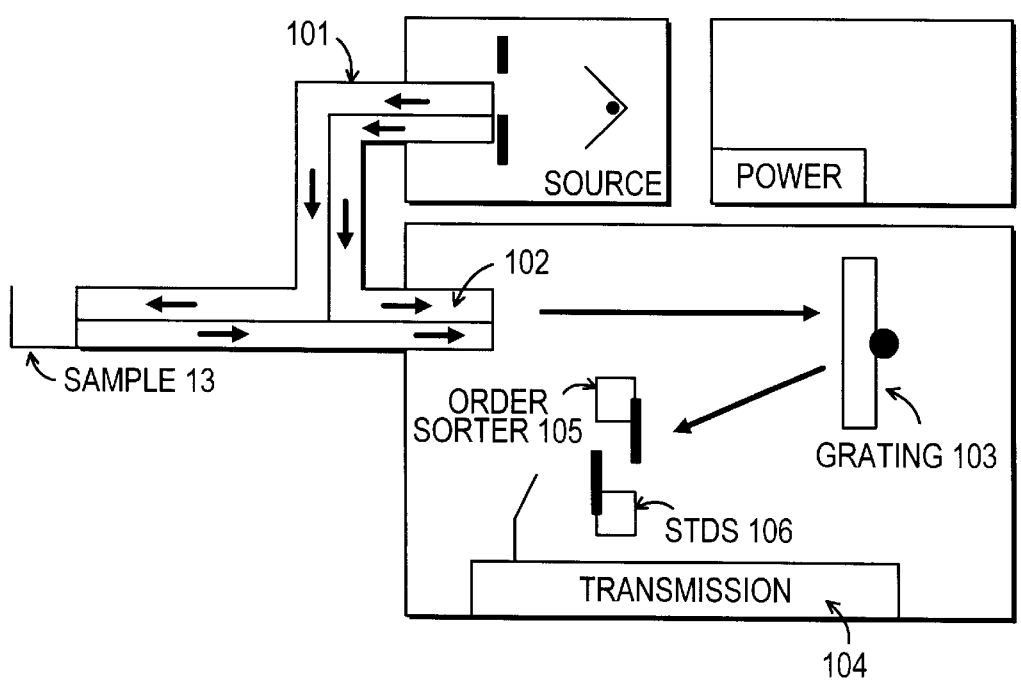
FIG. 10 shows a post-dispersive monochromator-based instrument in which the light is dispersed after striking the sample.

FIG. 10 shows a schematic diagram of a typical post-dispersive monochromator. This type of instrument provides the advantage of allowing the transmission of more energy on the sample via either a single fiberoptic strand or a fiberoptic bundle. Referring to FIG. 10, white light is piped through the fiberoptic strand or fiberoptic bundle 101 and onto the sample 13. The light is then reflected 102 off the sample 13 and back to the grating 103 (the dispersive element). After striking the grating 103, the light is separated into the various wavelengths by order sorting 105 and stds 106 components prior to striking a detector 104. The post-dispersive monochromator can be used with reflectance detectors.

The dedicated dispersive (grating-type) scanning NIR instruments, like those described above, vary in optical design but generally have the common features of tungsten-halogen source lamps, single monochromator with a holographic diffraction grating, and uncooled lead sulfide detectors.

Figure 11:
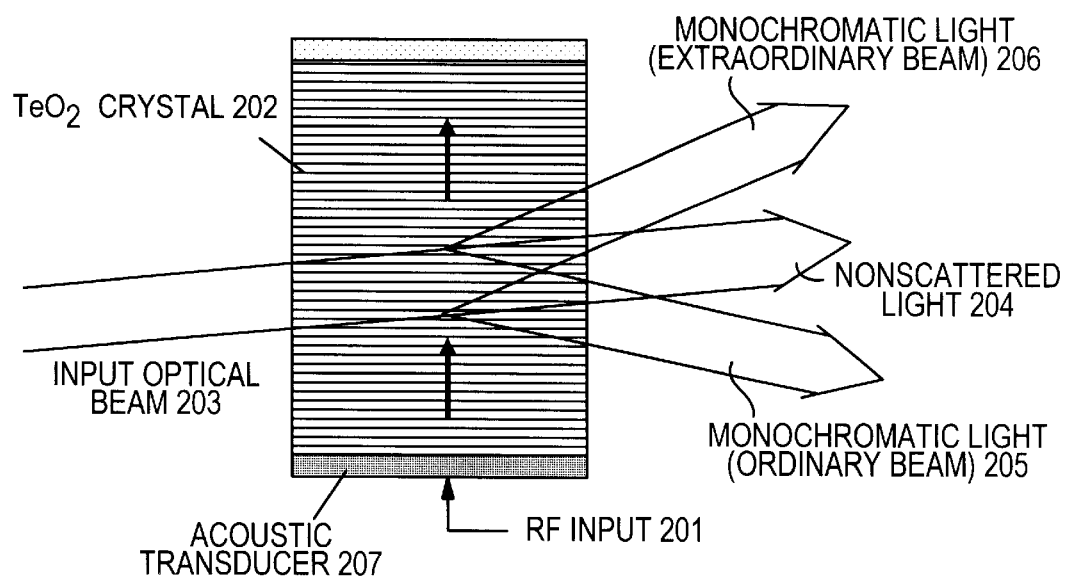
FIG. 11 illustrates an Acousto Optical Tunable Filter spectrometer.

FIG. 11 depicts an Acousto Optical Tunable Filter spectrometer utilizing an RF signal 201 to generate acoustic waves in a $TeO_2$ crystal 202. A light source 203 transmits a beam of light through the crystal 202, and the interaction between crystal 202 and RF signal 201 splits the beam of light into three beams: a center beam of unaltered white light 204 and two beams of monochromatic 205 and orthogonally 206 polarized light. A sample 13 is placed in the path of one of the monochromatic beams. The wavelength of the light source is incremented across a wavelength band of interest by varying the RF frequency.

On one surface of the specially cut crystal an acoustic transducer 207 is bonded. The acoustic transducer is a piezoelectric material, such as $LiNbO_3$ driven by 1–4 W of radio frequency (RF) coupled into the transducer. The high-frequency (30–200 MHz) acoustic waves induce index of refraction waves in the acoustooptical material. The waves travel through the crystal very quickly. Typically, within 20–30 $\mu$sec the acoustic waves "fill" the crystal, interacting with the broad-band light traveling through the crystal. The angles of the crystal axis, the relative angles of the broad-band light into three beams. As noted above, the center beam is the unaltered white light traveling through the crystal. The $TeO_2$ material has virtually no absorption from the visible spectrum all the way to about 5 $\mu$m. The two new beams generated by the acoustically excited crystal are, as discussed above, monochromatic and orthogonally polarized. These beams are used as monochromatic light sources for analytical purposes.

The main advantage of the AOTF optics is that the wavelength is electronically selected without the delays associated with mechanical monochromators. The electronic wavelength selection allows a very high-duty cycle because almost no time is wasted between wavelength switching. In comparison with "fast-scanning" instruments, the advantage is not only that the scanning rate is orders of magnitude faster but also that the wavelength access is random. If only four or five selected wavelengths are required for the concentration equation, the AOTF instrument is able to select those and is not confined to accessing all wavelengths serially (as in fast grating monochromators) or multiplexed (as in FT-NIR).

Besides the speed and efficiency of wavelength selection, the AOTF instruments generally are much smaller than grating monochromators but with equal resolution. In a properly engineered design, the long-term wavelength repeatability also surpasses that of the grating monochromator.

Figure 12A:
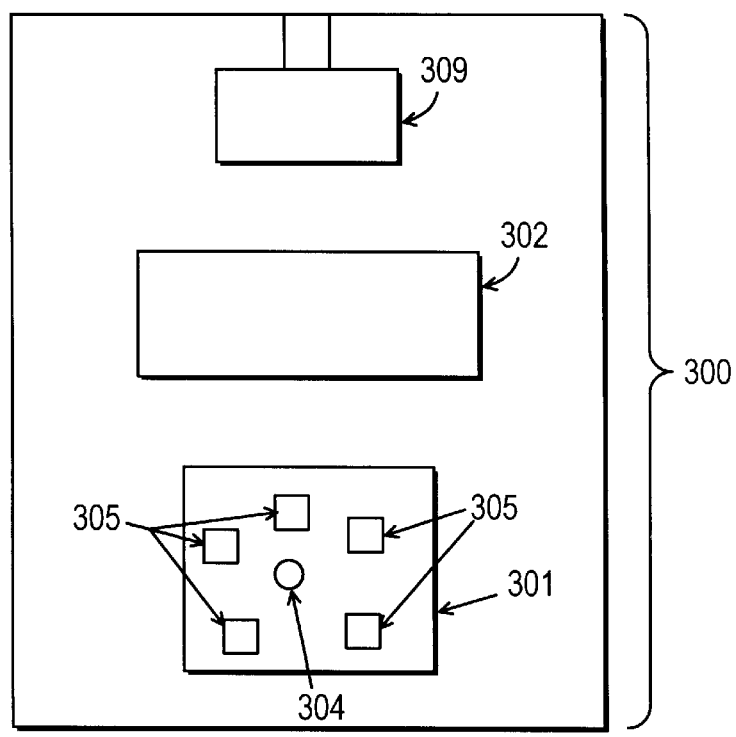
FIGS. 12A and 12B illustrates a noninvasive near IR spectral device that can be used for obtaining spectral scans.
Figure 12B:
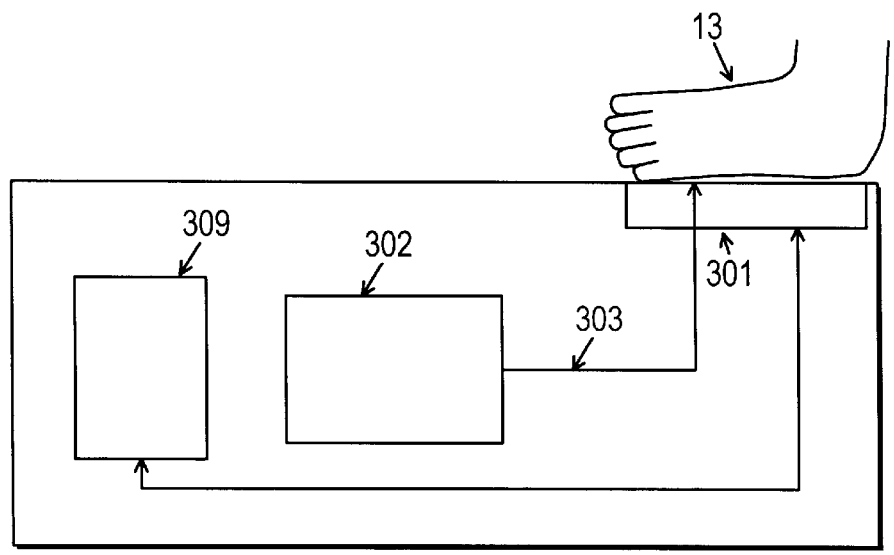

FIGS. 12A and 12B depict a preferred remote spectrometer 300 for performing noninvasive spectral scans of a sample 13 (i.e., the base of the thumb) to predict blood glucose levels. As shown in FIG. 12A, sample portion 30 includes a light emitting portion 304 and a plurality of detectors 305 surrounding light emitting portion 304. As shown in FIG. 12B, light emitting portion 301 of the sample module is connected by a fiber optic cable 303 to the monochrometer 302 comprising a light source and a grating for selecting desired wavelength (e.g., 1100–2500 nm). A communication module 309 receives spectral scans from the detectors 305 in sample portion 301 and transmits the spectral scan data to a remote computer (not shown). The communication module may also be configured to store the spectral scan data for subsequent use.

Figure 12C:
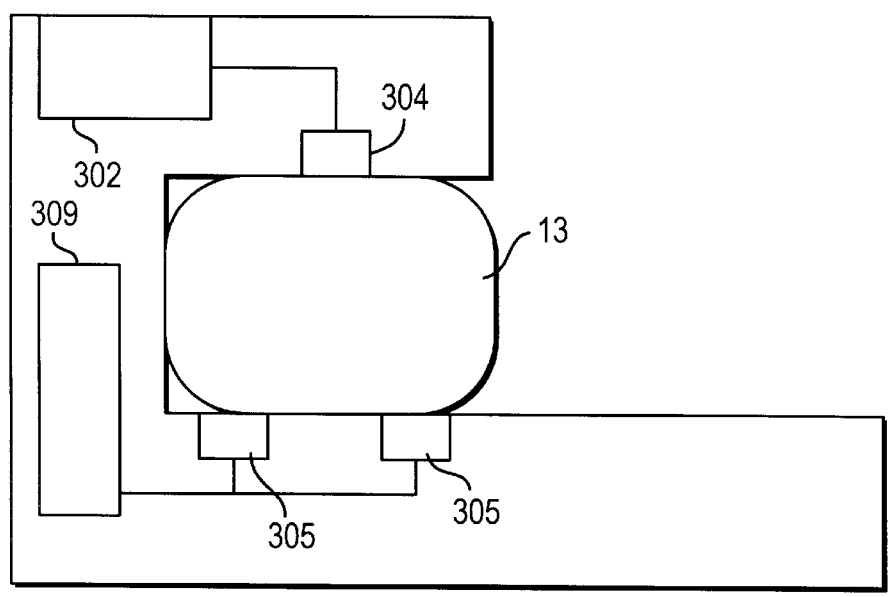
FIG. 12C illustrates another non-invasive near IR spectral device that can be used for obtaining spectral scans.

The spectrometer 300 of FIG. 12C is similar to the spectrometer 300 of FIGS. 12A and 12B, except that light emitting portion 304 is located above the five detectors 305, and the sample 13 (in this case, the base of the thumb) is placed between light emitting portion 304 and detectors 305.

Once the remote computer obtains the spectral scan, the spectral scan will then be stored in the memory on the computer. The remote computer will then automatically access the central computer, establish a communication link and then upload the spectral scan to the central computer. Alternatively, the remote spectrometer 300 itself may itself include a processor, a memory and a communications port for uploading the spectral data to the central computer.

The central computer is preferably a server or workstation capable of holding spectral databases for a plurality of patients. The workstation is preferably configured to allow multiple clients to concurrently access the server. Any known WAN networking technology may be used to promote this functionality. For each client, the central computer will store: 1) all spectral data collected from that client; 2) all constituent data from that client (from the invasive blood-monitoring device); and 3) the current modeling equation that is being used to predict the blood glucose level from the spectral scan. In preferred embodiments, the central computer also stores non-spectral compensation data and may further store additional information submitted by the patient, such as dietary intake and exercise regimen.

The central computer, in one embodiment, receives a plurality of spectral scans from the spectral device (remote or otherwise) and associated constituent data (invasively-measured blood glucose levels) from an invasive measurement device, and calculates the modeling equation from which future blood glucose levels will be predicted, preferably using the preferred technique discussed above.

The central computer then receives spectral data from a remote spectral device and, if the spectral scan is within the range of the modeling equation, predicts a blood glucose value from the modeling equation and sends the blood glucose value back to the patient. The central computer may also alert the patient when, based on the spectral data, the modeling equation is no longer valid, and either sends a message to the patient to attempt another reading or sends a message to begin a recalibration procedure. The central computer may also instruct the patient to begin a recalibration procedure at regular intervals (e.g., once a month). Once recalibration is initiated, the patient will perform a number of spectral scans and corresponding invasive measurements (to obtain constituent values) at designated times. The spectral data and constituent values are uploaded to the central computer, and the central computer then regenerates the modeling equation based on the original data as well as on the data uploaded during the recalibration procedure. As described above, in some instances it may be necessary to regenerate the modeling equation based only on new data. In this case, the patient will be instructed to take a sufficient number of invasive and noninvasive measurements to obtain a completely new modeling equation. Preferably, the central computer transmits the appropriate timing schedule to the patient via communication with the remote computer or the remote spectrometer 300. In this regard, additional instructions, such as medication schedules, may be transmitted to the patient in the same manner.

In another embodiment, the central computer regenerates a modeling equation for an individual patient, as described above and transmits the modeling equation to the portable unit containing a microprocessor and spectral device (and preferably an acceptable invasive blood glucose monitor). The patient can then conduct further noninvasive testing on a pre-determined schedule, with the portable unit itself predicting the individual's blood glucose using the modeling equation previously downloaded from the central computer. The spectral data can then be subsequently sent to the central computer for analysis. If the spectral data is not within an acceptable parameter a message is sent to the patient to regenerate (i.e., recalibrate) a modeling equation. The determination of whether the data is within acceptable parameters may be made by the portable unit itself, or alternatively by the central computer. Regeneration can also be initiated at regular predetermined intervals (such as monthly). As described above, regeneration may be initiated either partially or fully with new data, depending on the particular situation.

As set forth above, in certain preferred embodiments, the central computer is capable of transmitting basic instructions to the patient to obtain blood glucose levels or to take medication. In further embodiments, more complicated instructions can be sent to the patient, such as instructions to call the patient's doctor for reevaluation of medication or instructions to adjust medication regimen, diet or exercise.

Preferably, the data received by the central processing unit and the data sent back to the remote spectral device is time/date stamped and is secured (e.g., encrypted, requiring a key to decipher, or transmitted over a dedicated line and requiring a password for access).

Preferably, in those embodiments in which the unit containing the remote spectral device (or a remote computer) performs certain data storage and glucose prediction functions, all information obtained during the scanning is nevertheless submitted to the central computer for analysis and to ensure that regeneration of the modeling equation is not necessary.

The operation of the central computer and the maintenance of the models from each patient are preferably overseen by trained staff members.

In certain embodiments, the central computer is further connected to one or more doctor's offices, hospitals or other patient care facilities, such as a nursing home or hospice. This enables communication of relevant information directly from the central computer to the doctor where the information can be monitored and become part of the standard file on a patient. The doctor may contact the central computer to obtain information regarding the blood glucose levels of the relevant patients or can request individual information regarding patients. In a preferred embodiment, the doctor is able to obtain information concerning patient information, such as heart rate, pulse, blood pressure, dietary intake and exercise regimen.

In certain embodiments, blood glucose information is automatically transmitted to the doctor by the central computer upon completion of the central computer's receipt and analysis of a particular patient's information (e.g., STAT samples). In other embodiments, the blood glucose information for all patients in the system is automatically transmitted to the patient's doctor at regular intervals, preferably twice a day. In other preferred embodiments, other relevant patient information, such as heart rate and blood pressure, also are automatically transmitted to the doctor.

In yet a further embodiment, the doctor is capable of transmitting instructions concerning patient care to the central computer, which instructions are both stored by the central computer in the patient's file and transmitted by the central computer to the patient's remote computer as a message.

In a further embodiment of the present invention, the central computer is associated with a website through which the data can be accessed by the patient and/or physician. The website may contain further information relating to disease state, including referral service, articles of interest, links to hospitals and links to diabetes related associations. In further embodiments, diabetes related equipment and supplies can be purchased through the website. In yet further embodiments, the website contains or is linked to a remote licensed pharmacy capable of receiving prescriptions and filling prescriptions.

In certain embodiment, access to a patient's records is obtained through a secure line by entering a predesignated password. In other embodiments, patient information supplemental to blood glucose levels, such as information on exercise and dietary regimen, heart rate and pulse, can be digitally transmitted to the website by modem or by e-mail.

The method of the present invention, although described above in terms of the measurement of blood glucose, can also be used to predict any known clinical chemistry, hematology, or immunology body fluid parameters, including, e.g., insulin levels.

EXAMPLES

The following non-limiting examples illustrate suitable methods according to the invention. It should be noted that the examples provided below are not meant to be exclusive.

Example 1

A clinical study of seven patients was conducted over five weeks. Testing occurred once a week, as discussed below. At each time point, a fingerstick was taken and read on a Hemo-Cue® blood glucose analyzer (invasive blood glucose level) to obtain a constituent value, and a near IR reading was taken at the base of the thumb (non-invasive spectral scan used to predict blood glucose level).

For each individual patient, readings were performed at various times in relation to eating. The first reading was taken in the morning following a fast of at least eight hours. Immediately following the taking of the first reading, the patients ate a full meal. The second reading was taken at approximately 30 minutes after eating. Subsequent readings were taken approximately every 30 minutes up to and including 150 minutes after eating for a total of six readings (in some instances, a seventh reading was taken at 180 minutes after eating).

The near IR reading was taken with a model AP 1365-II Rapid Content Analyzer (RCA system), including a Model 6500 scanning Near-Infrared spectrometer. Each patient placed the base of his/her thumb on the Rapid Content Sample Module of the device (which included four detectors disposed about a source of NIR radiation).

The RCA system was manufactured by FOSS-NIR Systems and has the following specifications:

| Monochromator System | |
|---|---|
| Model Number | Wavelength Coverage |
| AP-1365-II | Model 6550 monochromater with 400–2500 nm coverage |
| Rapid Conent ™ Analyzer (RCA) Specifications | |
| Scan Rate | 1.8 scans/second |
| Wavelength Range | 1100–2500 nm (Standard Mode) 400–2500 nm (Wide-Range Mode) |
| Wavelength Accuracy | ±0.3 nm (Basis: Polystyrene Standard peaks 1100–2500 nm) |
| Wavelength Repeatability | ±0.010 nm (Standard Deviation of 10 consecutive scans 1100–2500 nm) |
| Noise (peak-to-peak) | <3.0 (400–700 nm)<0.4(700–2500 nm) |
| Noise (RMS Avg) | <0.2 (400–700 nm)<0.04(700–2500 nm) |
| Spectral Bandwidth | 10 ± 1 nm |
| Photometric Range | 3.0 Au (1100–2500 nm) |
| Linearity (2% to 99% reflectivity or transmissivity) | ±1.0% |
| Stray Light | <0.1% at 2300 nm |
| Operating Temperature Range | 15° C. to 33° C. (60° F. to 92° F.) |
| Power Consumption | 150 watts (maximum) |

The patients in the clinical study have the following profiles:

| Patient | Description |
|---|---|
| OMF | Elderly Diabetic Afro-American Female |
| MLM | Middle Aged Diabetic Caucasian Female |
| SLH | Middle Aged Diabetic Caucasian Female |
| SLR | Young Diabetic Caucasian Female |
| TFD | Middle Aged Diabetic Afro-American Male |
| BDD | Young Diabetic Caucasian Male |
| PFK | Young Caucasian Female (Control) |

Patient SLR dropped out of this clinical study for medical reasons that are not relevant here.

Criteria for Evaluation

For each patient, the spectral data and associated constituent values were randomly divided into a calibration set and a validation set, with approximately equal numbers of readings in each set. Two successive data transforms were then applied to the spectral data in the calibration and validation sets. The following is a list of the data transforms applied: NULL, ABS2REFL, NORMALIZ, FIRSTDRV, SECNDDRV, MULTSCAT, KUBLMUNK, SMOOTHNG, RATIO, MEANCNTR, SGDERIV1 and SGDERIV2. If a RATIO transform is selected, both numerator and denominator transforms are also selected from this list (except that neither may itself be a ratio). FIGS. 21A,B (clear transmittance) identify the manner in which the transforms were applied, except that the BASECORR transform was not used in the Study.

Some of the transforms, particularly the smoothing transform and derivative transforms, have parameters (e.g., spacing of data points for the first derivative, second derivative and smoothing transforms) associated with them. During the automatic search, for any data transform that requires a parameter, the data transform is performed multiple times, using different values of the parameter. The values used for each data transform requiring a parameter are presented in FIG. 22.

The following algorithms were then applied to each set of transformed spectral scan: PLS (partial least squares), PCR (principal component regression), and MLR (multiple linear regression), thereby producing three equations for each set of transformed spectral scan. Each of the equations (or calibration models) is then applied to the spectral data in the validation set.

The "best" modeling equation was selected on the basis of a "Figure of Merit", which is computed using a weighted sum of the SEE and SEP, the SEP being given twice the weight of the SEE. The FOM was calculated using the following equation, wherein "Bias in FOM" is unchecked:

$$FOM = \sqrt{(SEE^2 + 2*SEP^2)/3} ,$$

where:
SEE is the Standard Error of Estimate from the calculations on the calibration data; and
SEP is the Standard Error of Estimate from the calculations on the validation data.

When all calculations have been completed, the results are sorted according to the Figure of Merit (FOM), and the equation corresponding to the data transform and algorithm providing the lowest value for the FOM is determined and designated as the best equation.

Results and Discussion

Table I summarizes the best modeling equation as calculated for each patient, based on the FOM, using the first four weeks of readings (unless otherwise indicated in the Patients Results Summary, infra). These modeling equations were then used to predict the fifth week readings. The results are summarized below with reference to FIGS. 13–18.

TABLE I

| Patient | Wavelength (nm) | Transformation Applied | Spacing + Parameters Used | FOM |
|---|---|---|---|---|
| BDD | 1852, 2166, 2320, 2380, 2418 | Multiplicative scatter and 1$^{st}$ Derivative | spacing 1 | 0.91 |

TABLE I-continued

| Patient | Wavelength (nm) | Transformation Applied | Spacing + Parameters Used | FOM |
|---|---|---|---|---|
| MLM | 1482, 1550, 1934, 2184, 2284 | 2nd Derivative and Normalization | | 0.57 |
| OMF | 1248, 1268, 1292, 2138, 2358 | Null and Ratio (1st Derivative/1st Derivative) | ratio spacing 6 | 0.91 |
| PFK | 1384, 1496, 2058, 2236, 2384 | Null and Ratio (2nd Derivative/2nd Derivative) | ratio coefficient: 42, 5, 0, −3, −4, −3, 0 and 5 | 0.82 |
| SLH | 1187, 1287, 1403, 1519, 1775 | Smoothing and 2nd Derivative | Smoothing factor 8 Spacing 2 | 0.87 |
| SLR | 1292, 1362, 1388, 1830, 1894 | Null and Ratio (2nd Derivative/2nd Derivative) | ratio spacing 12 | 0.87 |
| TFD | 1268, 1856, 1882, 2298, 2340 | Null and Ratio (2nd Derivative/2nd Derivative) | ratio spacing 12 | 0.70 |

Patient Results Summary

In all female patients, there was evidence of the blood glucose levels being in "control." That is, the patient begins each day in a fasting mode, eats breakfast, then has blood glucose measurements taken at ½ hour increments for 2 ½ hours. If the blood level follows a pattern of glucose levels from week to week or day to day, the patient is said to be "in control" or "under control." That is, if the fasting patient's blood glucose rises after eating, peaks two hours later, then begins to decline with each subsequent test, he/she is "in control." This does not mean that the absolute levels are the desirable ones for health, merely that they are repetitive from day to day and week to week.

Figure 13A:
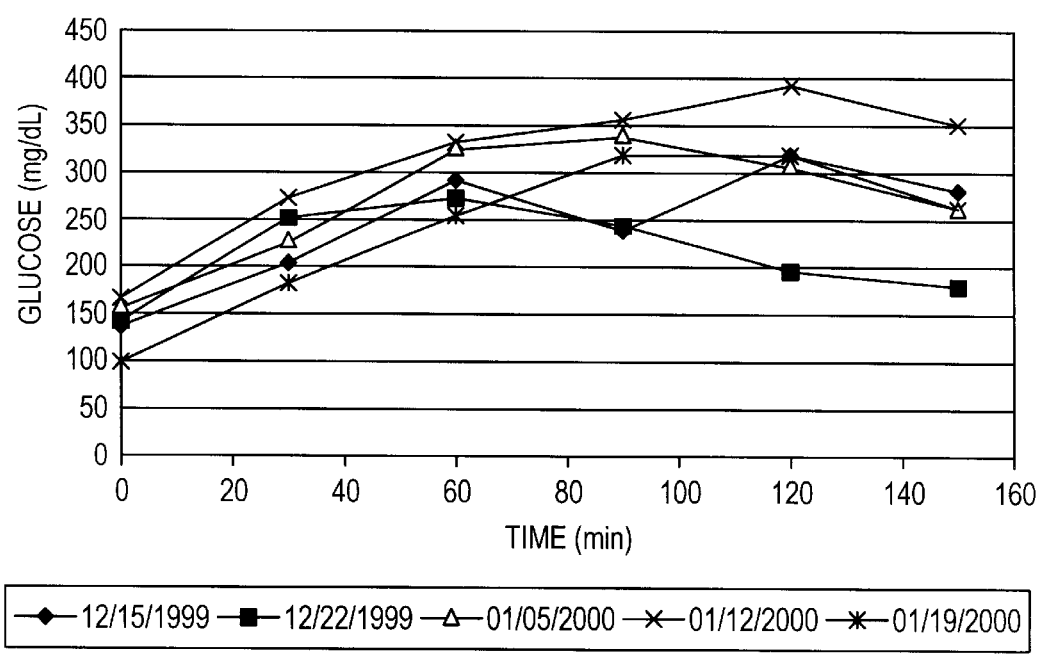
FIG. 13A illustrates the blood glucose profile of an elderly diabetic Afro-American female (patient OMF).
Figure 13B:
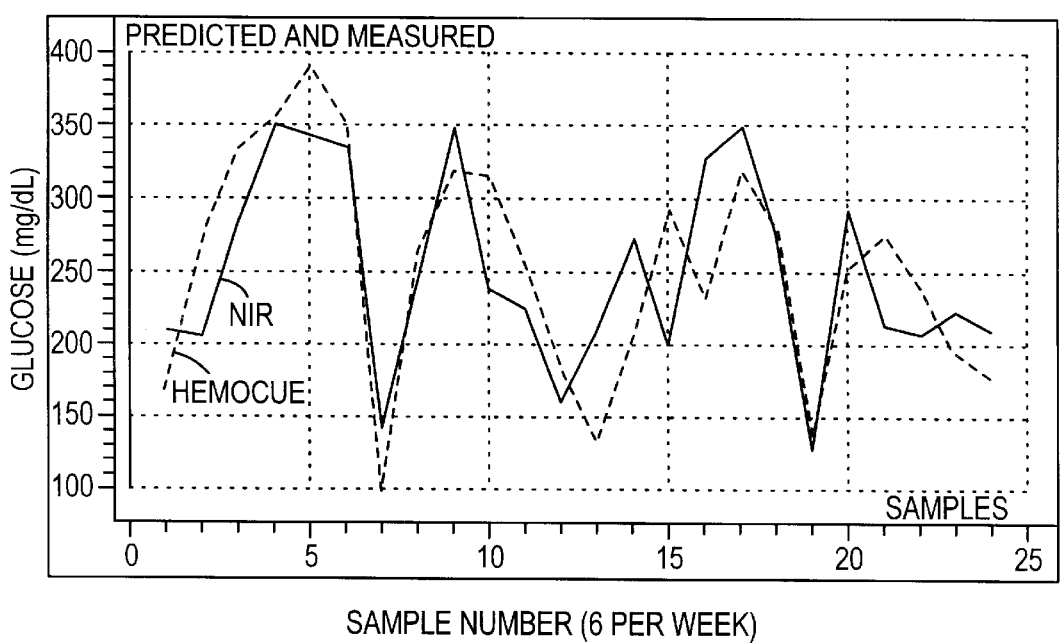
FIG. 13B illustrates a modeling equation of near infrared values versus noninvasive glucose values using a Hemo-Cue® system for patient OMF.
Figure 13C:
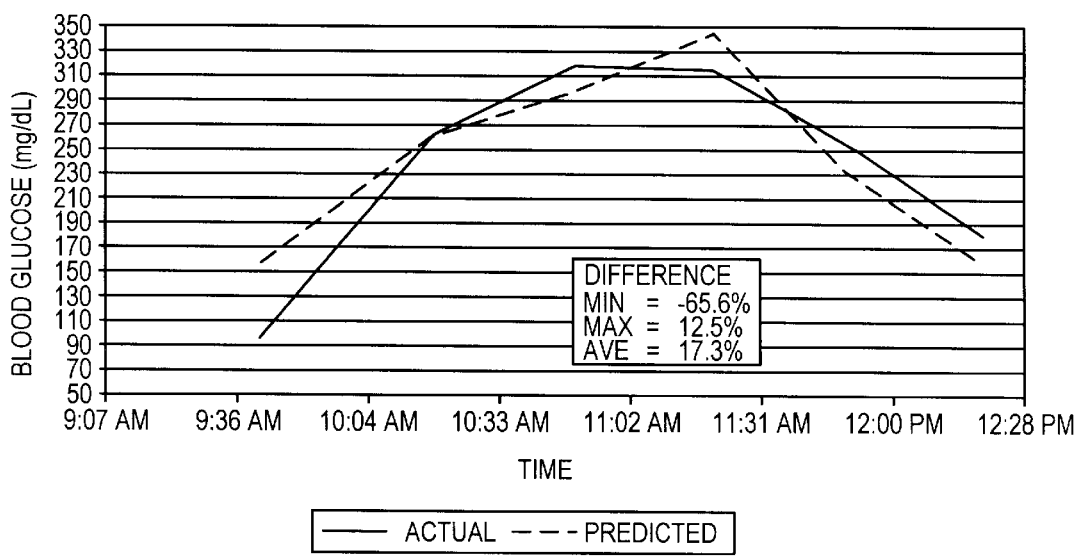
FIG. 13C illustrates a comparison of NIR glucose values (dashed line) versus Hemo-Cue® system glucose values (solid line) for patient OMF.

An example of a controlled patient's blood glucose data is seen in FIGS. 13A–C. In this graphic, FIG. 13A shows the blood glucose profile of patient OMF, an elderly, female Afro-American diabetic, who is seen to be in control because her pattern is nearly identical each week of the five-week test. When a Multiple Linear Regression equation was generated for this patient, the NIR calculated results were quite comparable with the reference values from the Hemo-Cue® tester. A comparison of the NIR calculated values (dashed line) versus the Hemo-Cue® reference values (solid line) is shown in FIG. 13B.

The values for the fifth week were calculated using an equation built from the first four weeks' data as an external validation test. That is, the spectral scans taken on the fifth week were analyzed by the modeling equation, and glucose values were generated. These values (dashed line) are compared with the reference (Hemo-Cue®) values (solid line) in FIG. 13C. As can be seen, the rise and fall of the blood glucose is followed reasonably well. What is seen is the correlation to the invasive meter that is measuring glucose in blood, specifically, using an enzyme/electrochemical process.

Figure 14A:
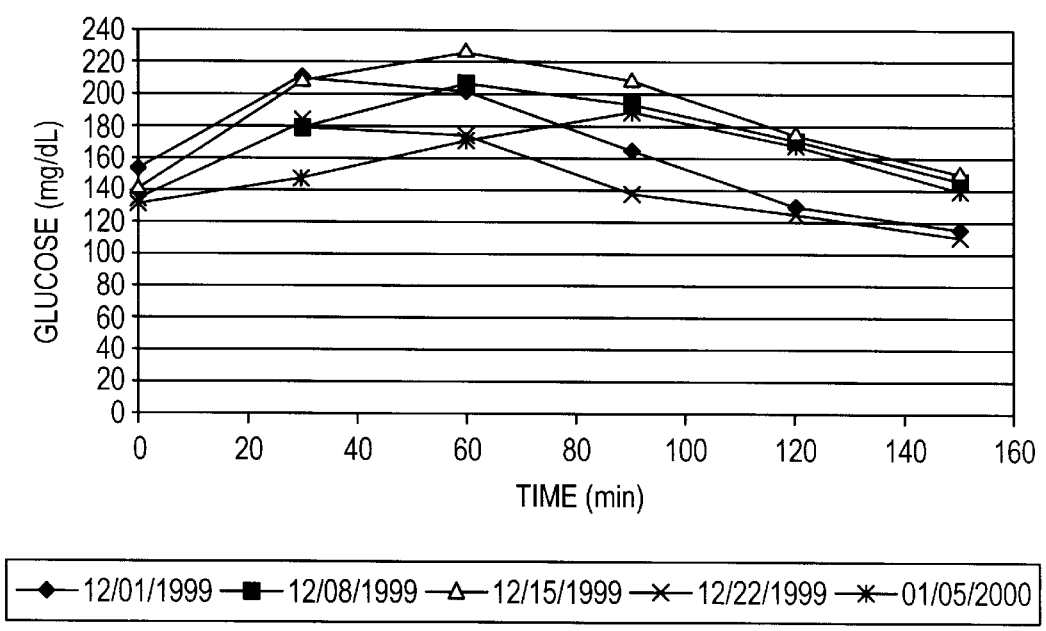
FIG. 14A illustrates the blood glucose profile over five weeks of a middle-age diabetic Caucasian female (patient MLM).
Figure 14B:
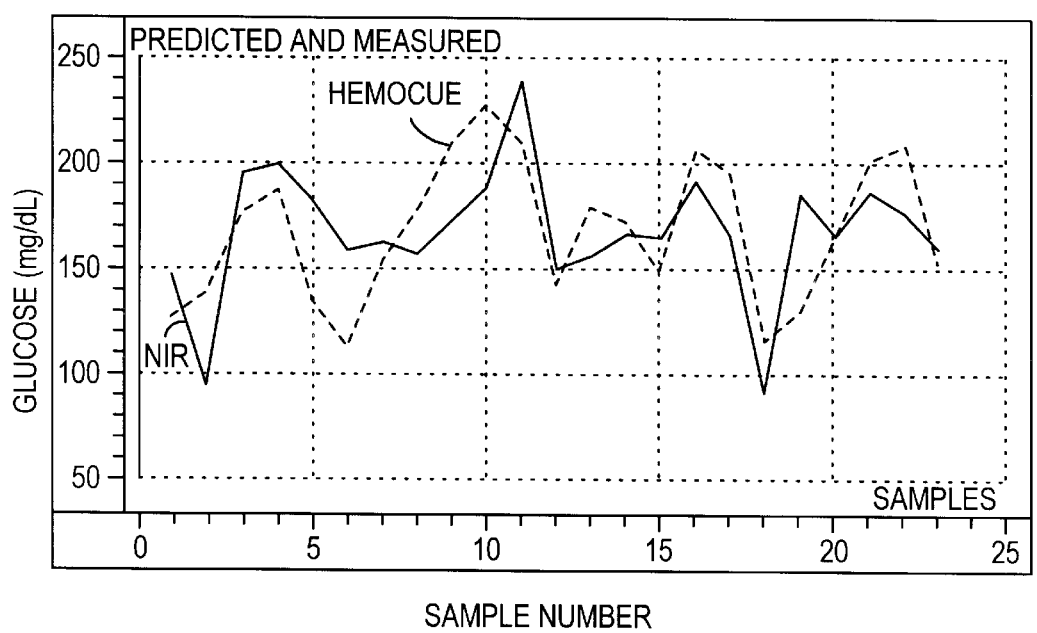
FIG. 14B illustrates a modeling equation of near infrared values versus noninvasive glucose values using a Hemo-Cue® system for patient MLM.
Figure 14C:
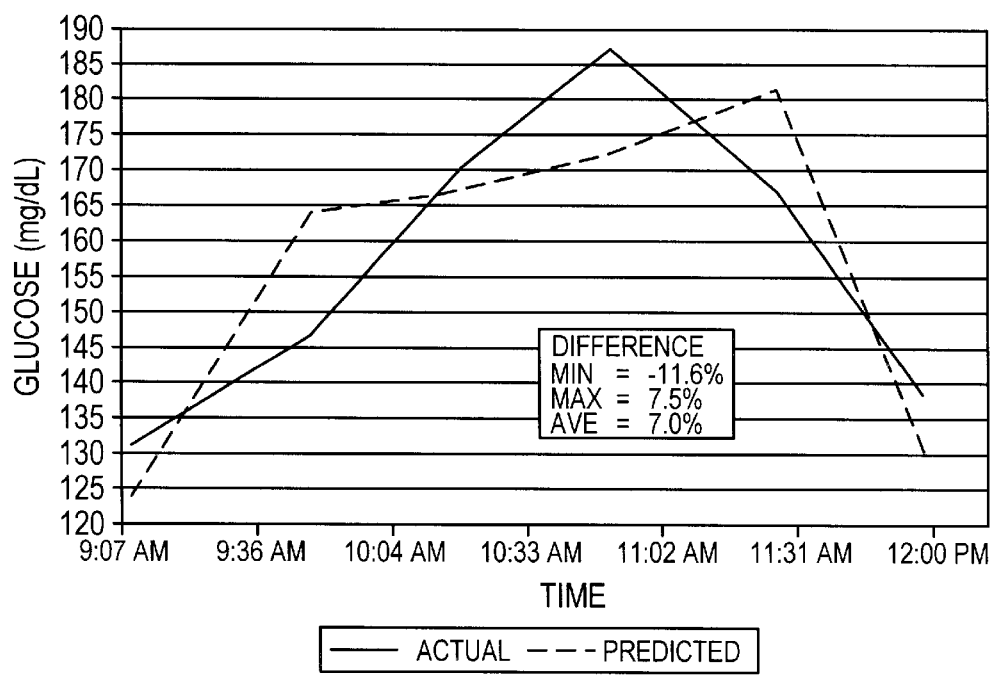
FIG. 14C illustrates a comparison of NIR glucose values (dashed line) versus Hemo-Cue® system glucose values (solid line) for patient MLM.

FIGS. 14A–C show the same experiment with a middle-aged female diabetic patient (MLM). This patient was similarly "in control" as can be seen from the five-week blood glucose profile in FIG. 14A, which shows that patient MLM's pattern was nearly identical each week of the five-week test. Again, the data tracked well, as can be seen in FIG. 14B, which shows a comparison of a Multiple Linear Regression equation generated for this patient based upon the NIR calculated values (dashed line) and based upon the Hemo-Cue® reference values (solid line). Similarly, FIG. 14C shows close correlation of the external validation test, i.e., that the spectral scans taken on the fifth week were analyzed by the modeling equation, and the generated glucose values (dashed line) are quite close to the reference (Hemo-Cue®) values (solid line). As can be seen from these figures, the NIR calculated results were quite comparable with the reference values from the Hemo-Cue® tester for patient MLM.

Figure 15A:
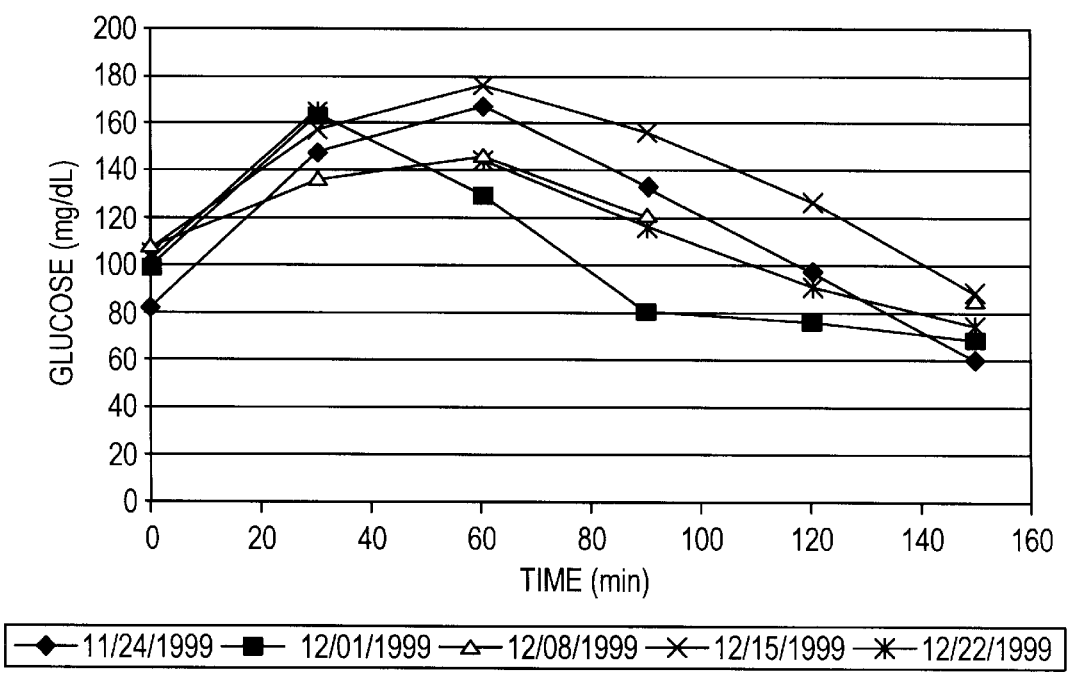
FIG. 15A illustrates the blood glucose profile over five weeks of a middle-age diabetic Caucasian female (patient SLH).
Figure 15B:
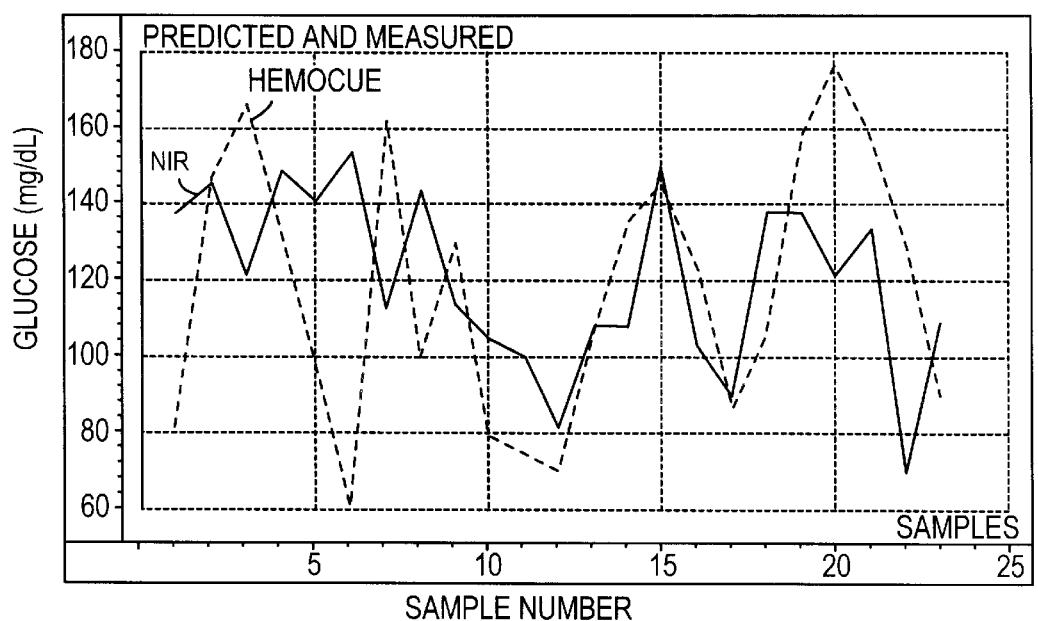
FIG. 15B illustrates a modeling equation of near infrared values versus noninvasive glucose values using a Hemo-Cue® system for patient SLH.
Figure 15C:
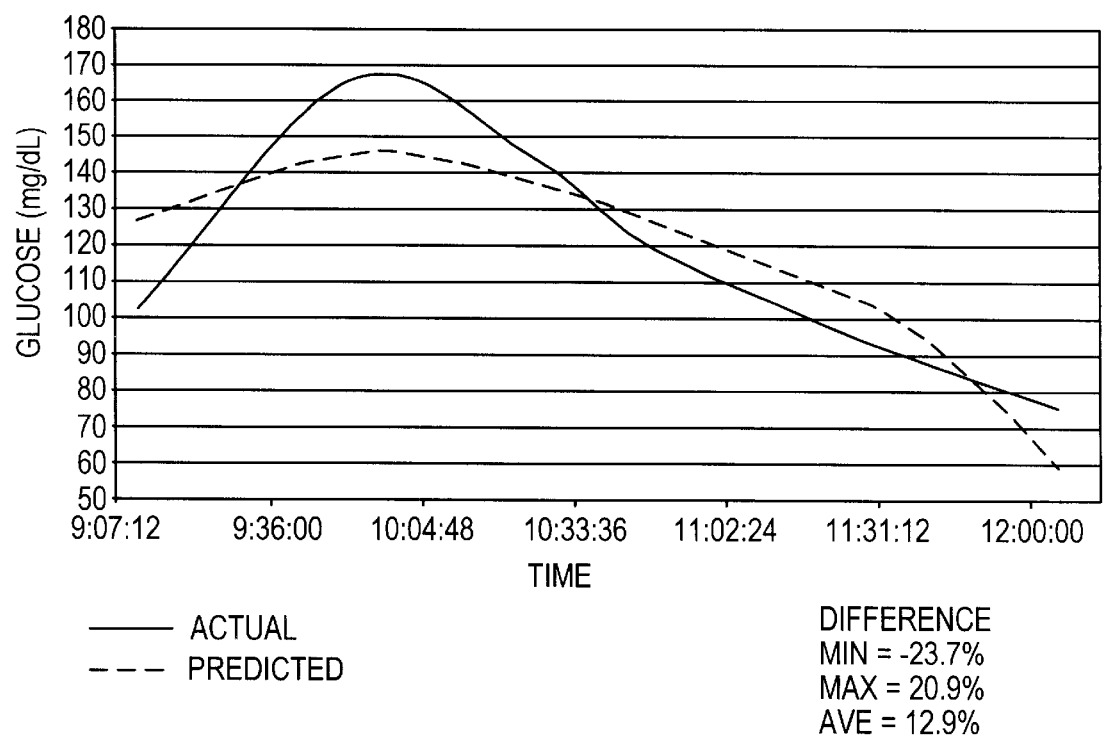
FIG. 15C illustrates a comparison of NIR glucose values (dashed line) versus Hemo-Cue® system glucose values (solid line) for patient SLH.

The results from a second middle-aged female patient (SLH) are shown in FIGS. 15A–C. Once again, an "in control" patient showed good results. Each of the five-week blood glucose profile shown in FIG. 15A was quite similar to the others. The comparison of a Multiple Linear Regression equation generated for this patient based upon the NIR calculated values (dashed line) and the Hemo-Cue® reference values (solid line) shown in FIG. 15B tracks well, and the fifth week external modeling equation validation test shown in FIG. 15C shows a close correlation. Thus, for patient SLH, the NIR calculated results were quite comparable with the reference values from the Hemo-Cue® tester.

Figure 16A:
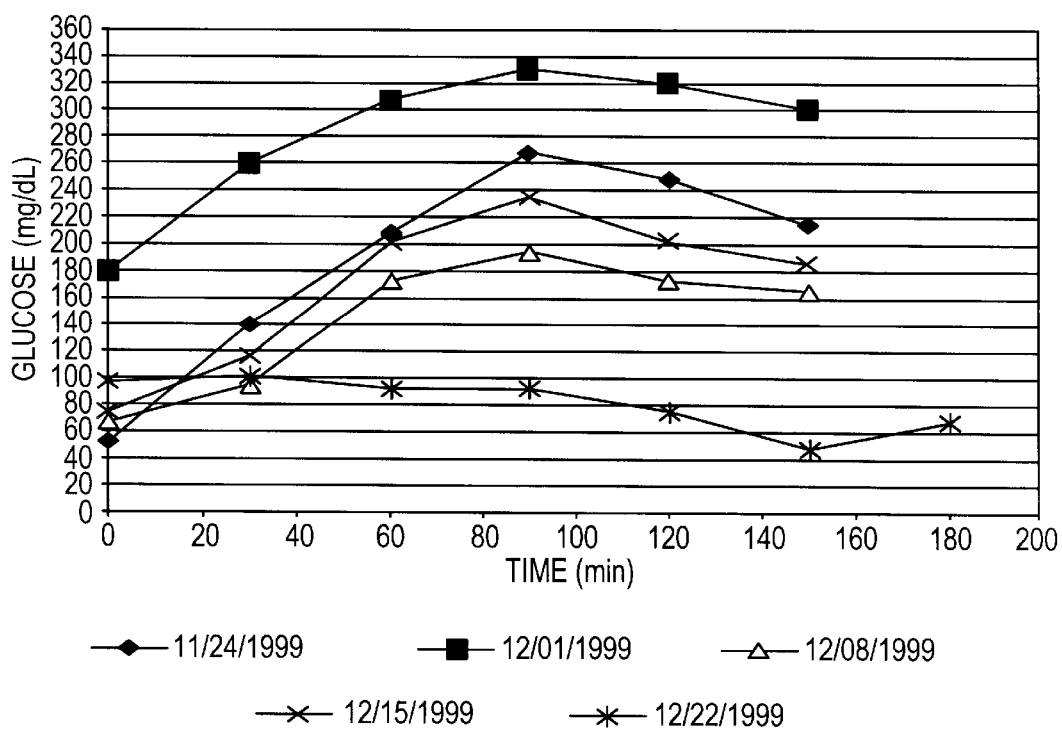
FIG. 16A illustrates the blood glucose profile over five weeks of a middle-age diabetic Afro-American male (patient TFD).
Figure 16B:
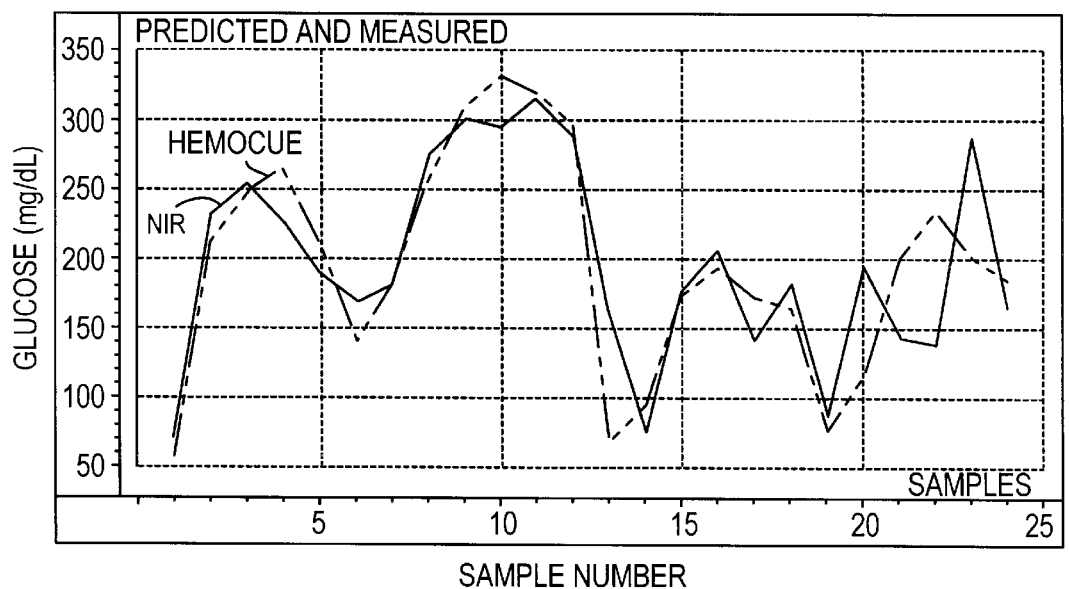
FIG. 16B illustrates a modeling equation of near infrared values versus noninvasive glucose values using a Hemo-Cue® system for patient TFD.
Figure 16C:
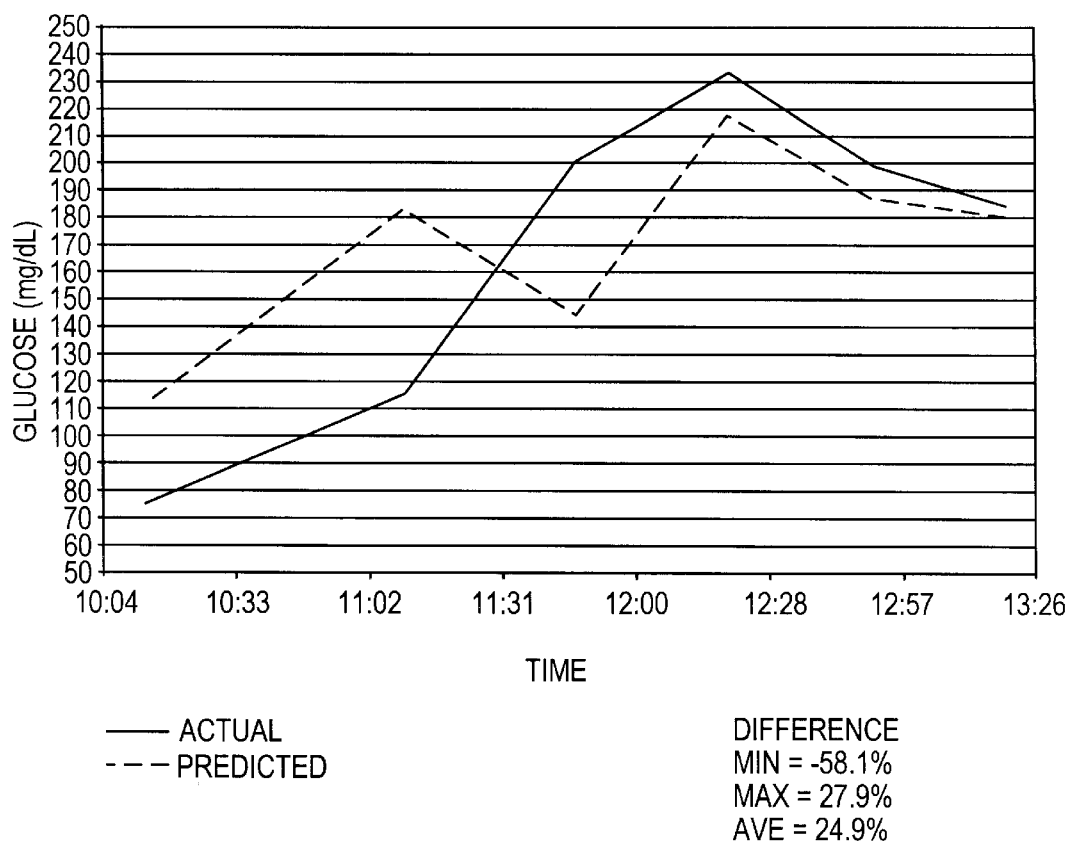
FIG. 16C illustrates a comparison of NIR glucose values (dashed line) versus Hemo-Cue® system glucose values (solid line) for patient TFD.

Patient TFD, a middle-aged Afro-American male diabetic, is clearly "out of control", as seen in FIGS. 16A–C. FIG. 16A shows that the patient's blood glucose levels are recorded within a wide range from a high of 330 mg/dL on week 2 to a low of 44 mg/dL on week 5. The blood glucose level predicted at week 5 represents a lower than normal value often associated with hypoglycemia. When the last week's data is eliminated, a reasonable prediction pattern is generated, wherein the NIR results closely resemble the reference values (FIG. 16C.)

Figure 17A:
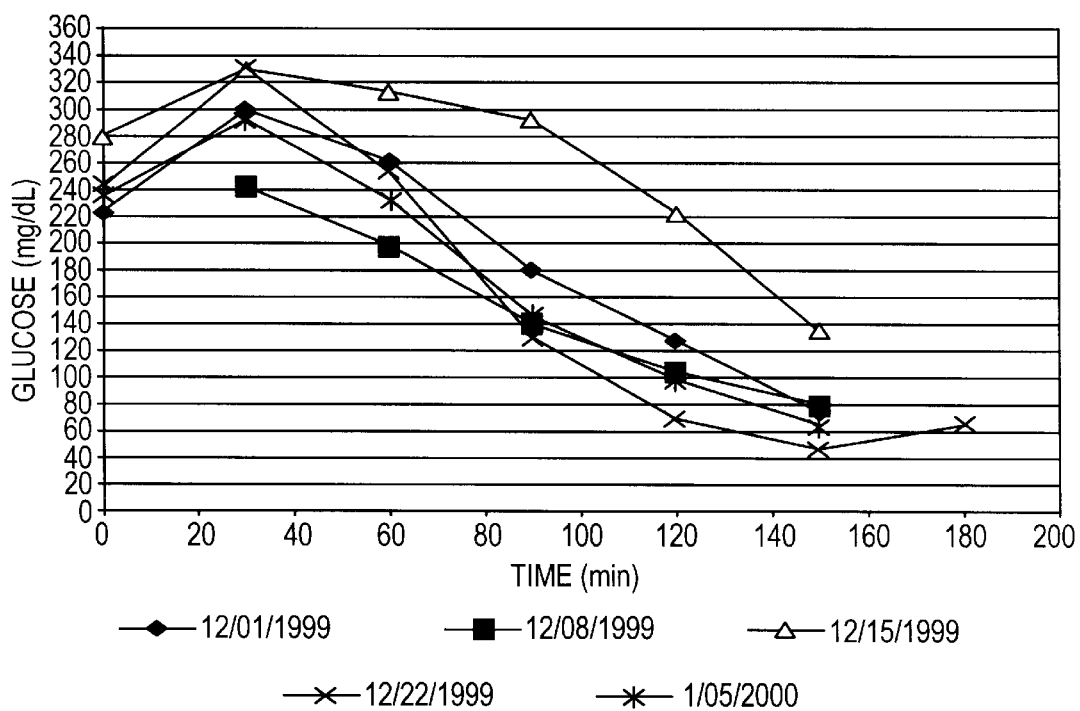
FIG. 17A illustrates the blood glucose profile over five weeks of a young diabetic Caucasian male patient BDD).
Figure 17B:
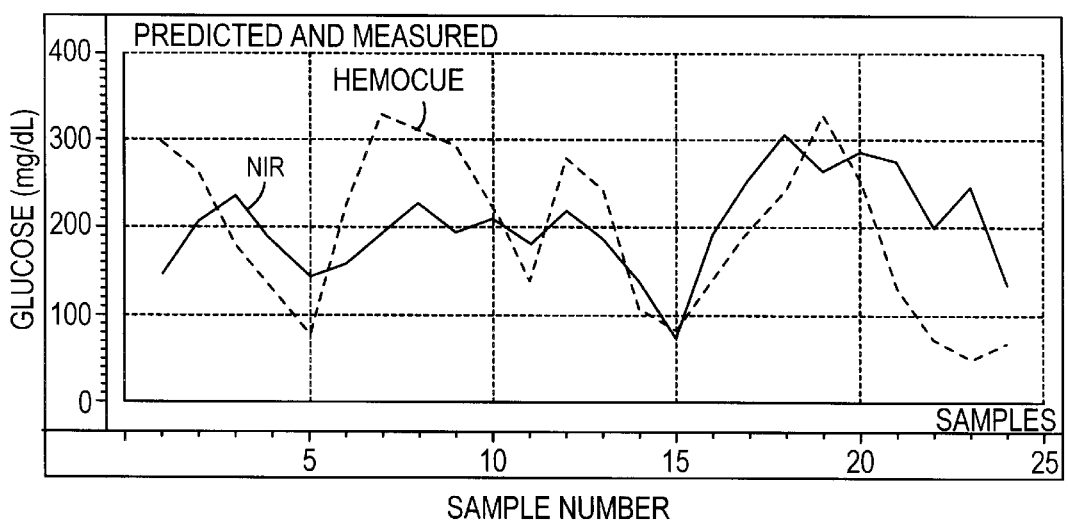
FIG. 17B illustrates a modeling equation of near infrared values versus noninvasive glucose values using a Hemo-Cue® system for patient BDD
Figure 17C:
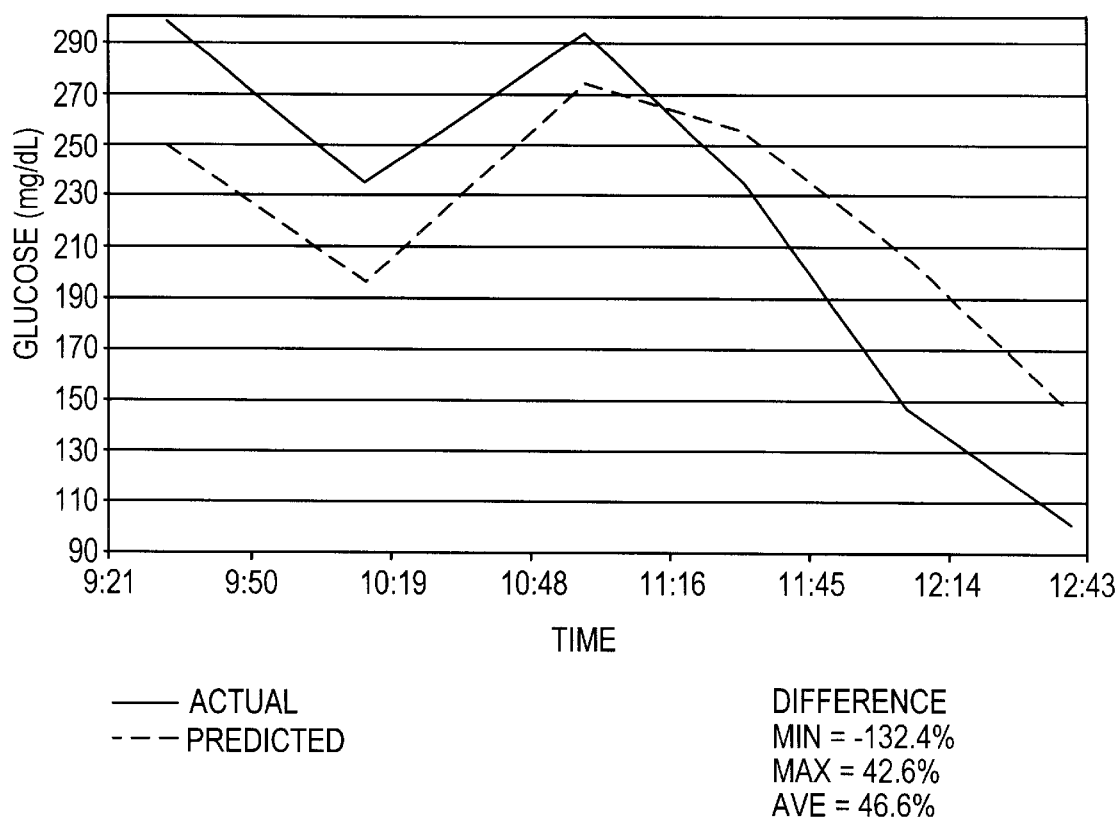
FIG. 17C illustrates a comparison of NIR glucose values (dashed line) versus Hemo-Cue® system glucose values (solid line) for patient BDD.

A similar decision was made for the data of BDD, a young male Caucasian diabetic, as shown in FIGS. 17A–C. It may be seen that week 3 values are clearly different from the values of the other four weeks (FIG. 17A). Using the first, second and fourth weeks to generate an equation (FIG. 17B), the fifth week's glucose values were calculated. FIG. 17C shows the agreement between the calculated and reference values for week 5.

Figure 18A:
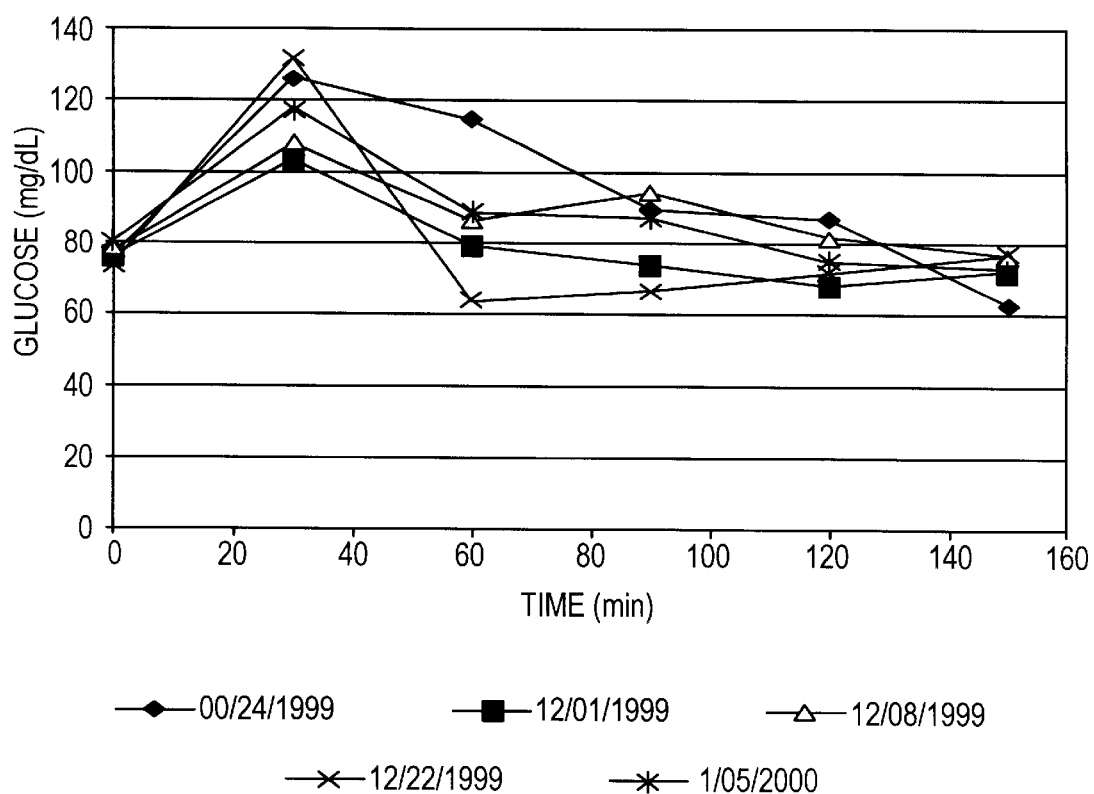
FIG. 18A illustrates the blood glucose profile over five weeks of a young Caucasian female (patient PFK), used as a control subject.
Figure 18B:
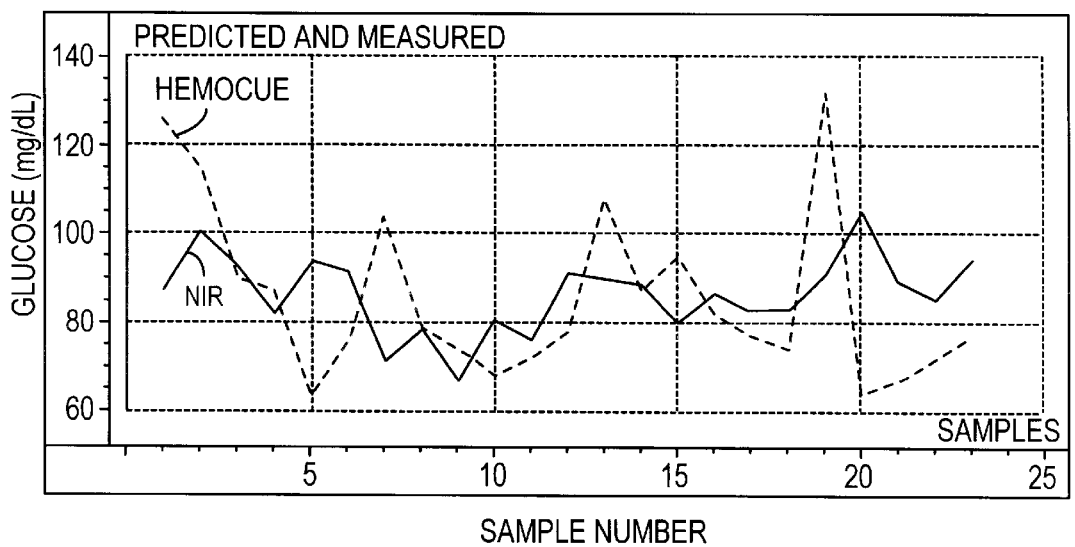
FIG. 18B illustrates a modeling equation of near infrared values versus noninvasive glucose values using a Hemo-Cue® system for patient PFK.
Figure 18C:
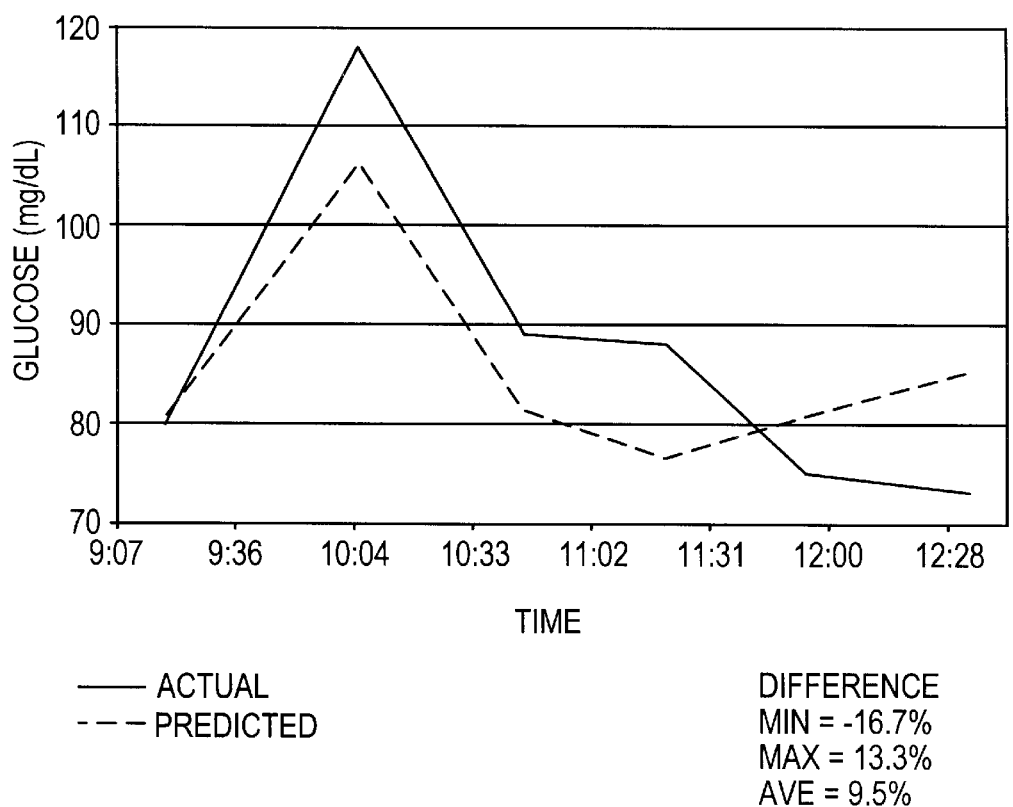
FIG. 18C illustrates a comparison of NIR glucose values (dashed line) versus Hemo-Cue® system glucose values (solid line) for patient PFK.

The single control for this study was a young, female Caucasian non-diabetic (PFK). FIG. 18A shows blood glucose levels of a healthy person. While the validation comparison with reference values (FIG. 18B) is not perfect, FIG. 18C shows very nice agreement between calculated and reference values for the fifth week. (The y-axis scaled is greatly reduced for this normal, healthy subject.)

Many other variations of the present invention would be obvious to those skilled in the art and are contemplated to be within the scope of the appended claims. One skilled in the art will appreciate that the present invention can be practiced by other than the described embodiments, which are presented for purposes of illustration and not limitation.

What is claimed is:

1. A method for predicting blood glucose values in a patient comprising:
  (a) generating an individualized modeling equation for a patient as a function of a plurality of first non-invasive spectral scans of a body part of the patient and an analysis of blood samples from the patient and storing the individualized modeling equation on a central computer;
  (b) receiving, from the patient, a second non-invasive spectral scan generated by a remote spectral device;
  (c) predicting a blood glucose value for the patient as a function of the second non-invasive spectral scan and the individualized modeling equation, and transmitting the predicted blood glucose value to the patient;

(d) if, based upon the second non-invasive spectral scan the modeling equation requires regeneration, transmitting a request for both a set of third non invasive spectral scans and a corresponding set of blood glucose values to the patient;

(e) acquiring the set of third noninvasive spectral scans from the patient using the remote spectral device and a corresponding set of blood glucose values from a remote invasive blood glucose monitor;

(f) transmitting the set of third noninvasive spectral scans and corresponding blood glucose values to the central computer; and (g) regenerating the individualized modeling equation as a function of the set of third noninvasive spectral scans and corresponding blood glucose values.

2. The method of claim 1, wherein the remote spectral device includes an infrared spectrometer.

3. The method of claim 2, wherein the infrared spectrometer is selected from the group consisting of a grating spectrometer, a diode array spectrometer, a filter-type spectrometer, an Acousto Optical Tunable Filter spectrometer, a scanning spectrometer, and a nondispersive spectrometer.

4. The method of claim 1, wherein the remote spectral device is handheld.

5. The method of claim 1, wherein the invasive method is selected from the group consisting of taking a blood sample by a venipuncture, a fingerstick, and a heelstick.

6. The method of claim 5, wherein the blood sample is inserted into an analytical device.

7. The method of claim 1, wherein the spectral device communicates with the central computer by a mode of data transmission.

8. The method of claim 7, wherein the mode of data transmission is one of a cellular data link, a telephone modem, a direct satellite link, an Internet link, or an RS232 data connection.

9. The method of claim 1, wherein the remote spectral device is one of a sensor, a monitor and a handheld computer.

10. The method of claim 1, wherein the remote spectral device detects nonspectral body properties.

11. The method of claim 1, wherein the remote spectral device controls administering an amount of a drug to the patient.

12. The method of claim 1, wherein the central computer is a workstation capable of holding a plurality of spectral scans and modeling equations for a plurality of patients.

13. An automated method for predicting blood glucose values using a noninvasive spectroscopic technique, comprising the steps of:

(a) taking a plurality of measurements of a patient's blood glucose levels using a noninvasive spectral device and an invasive glucose monitoring method;

(b) associating a constituent value measured by the invasive glucose monitoring method with the blood glucose level measured by the spectral device;

(c) dividing the plurality of spectral meausrements and constituent values into a calibration subset and a validation subset;

(d) transforming the spectral measurements in the calibration sub-set and the validation subset by applying a plurality of first mathematical functions to the calibration sub-set and the validation sub-set to obtain a plurality of transformed validation sub-sets and a plurality of transformed calibration sub-sets;

(e) resolving each transformed calibration data sub-set in step (d) by at least one of a second mathematical function to generate a plurality of modeling equations;

(f) selecting a best modeling equation of the plurality of modeling equations;

(g) storing the best modeling equation in a central computer;

(h) acquiring a spectral scan from the patient using a remote noninvasive spectral device;

(I) transmitting the spectral scan from step (h) to the central computer of step (g);

(j) if, based on the received spectral scan, the modeling equation does not require regeneration, predicting the patient's blood glucose level using the best modeling equation; and (k) if, based on the received spectral scan, the modeling equation requires regeneration, regenerating the best modeling equation based on the spectral scans and constituent values and a plurality of new spectral scans.

14. The method of claim 13, wherein the noninvasive spectral device includes a remote spectral device.

15. The method of claim 13, wherein the measurements are taken daily for about six weeks.

16. The method of claim 13 wherein the regenerating step further comprises the steps of:

(a) taking a plurality of invasive blood glucose levels and noninvasive spectral scans from the patient;

(b) transmitting the blood glucose levels and spectral scans of step (a) to the central computer; and (c) regenerating the modeling equation using the invasive blood glucose levels and non invasive spectral scans of steps (a) and (b).

17. The method of claim 16, wherein the regeneration is conducted about every four weeks.

18. The method of claim 2, wherein the best modeling equation is selected as a function of calculating a figure of merit (FOM), the FOM being defined as:

$$FOM = \sqrt{(SEE^2 + 2*SEP^2)/3}$$

where:
SEE is the Standard Error of Estimate from the calculations on the calibration data;
SEP is the Standard Error of Estimate from the calculations on the validation data;

and the modeling equation which provides the best correlation between the spectral data in the validation sub-set and the corresponding constituent values in the validation sub-set being identified as the modeling equation with the lowest FOM value.

19. The method of claim 2, wherein the at least one second mathematical function includes one or more of a partial least squares, a principal component regression, a neural network, and a multiple linear regression analysis.

20. The method of claim 2, Wherein the first mathematical functions include performing a normalization of the spectral measurement, performing a first derivative on the spectral measurement, performing a second derivative on the spectral measurement, performing a multiplicative scatter correction on the spectral measurement, performing smoothing transform on the spectral measurement, and performing a Kubelka-Munk function on the spectral measurement.

21. The method of claim 13, wherein the first mathematical functions are applied singularly and two-at-a-time.

22. A method for predicting blood glucose values in an individual patient, comprising:

generating, on a central computer, a modeling equation for predicting blood glucose values in a patient and predicting a blood glucose value for the patient based upon a plurality of first non-invasive spectral scans of the patient with a remote spectral device and the modeling equation;

if based on a second non-invasive spectral scan, the modeling equation requires regeneration, regenerating, on the central computer, the modeling equation based upon non-invasive spectral scans of the patient with the remote spectral device and corresponding constituent values for the patient based upon an invasive blood glucose measurement with a remote invasive device; and predicting a blood glucose value for the patient based upon a subsequent non-invasive spectral scan of the patient with the remote spectral device and the regenerated modeling equation.

23. A system for predicting blood glucose values in an individual patient, comprising a remote non-invasive spectral device, the remote non-invasive spectral device generating a spectral scan of a body part of a patient;

a remote invasive device, the remote invasive device generating a constituent value for the patient; and a central computer, the central computer storing a modeling equation for predicting blood glucose values in a patient, the central computer predicting a blood glucose value for the patient based upon a plurality of first non-invasive spectral scans of the patient from the remote non-invasive spectral device and the modeling equation, if based on a second non-invasive spectral scan, the modeling equation requires regeneration the central computer regenerating the modeling equation based upon a plurality of third non-invasive spectral scan of the patient from the remote non-invasive spectral device and a corresponding plurality of constituent values for the patient from the remote invasive device, and predicting a blood glucose value for the patient based upon a subsequent non-invasive spectral scan of the patient with the remote non-invasive spectral device and the regenerated modeling equation.

* * * * *